US012606837B2

(12) United States Patent
Arai et al.

(10) Patent No.: US 12,606,837 B2
(45) Date of Patent: Apr. 21, 2026

(54) MUTANT FILAMENTOUS FUNGUS, AND METHOD FOR PRODUCING PROTEIN USING SAME

(71) Applicant: Kao Corporation, Tokyo (JP)

(72) Inventors: Toshiharu Arai, Wakayama (JP); Sakurako Ichinose, Wakayama (JP)

(73) Assignee: Kao Corporation, Tokyo (JP)

( * ) Notice: Subject to any disclaimer, the term of this patent is extended or adjusted under 35 U.S.C. 154(b) by 918 days.

(21) Appl. No.: 17/777,658

(22) PCT Filed: Nov. 13, 2020

(86) PCT No.: PCT/JP2020/042489
§ 371 (c)(1),
(2) Date: May 18, 2022

(87) PCT Pub. No.: WO2021/100631
PCT Pub. Date: May 27, 2021

(65) Prior Publication Data
US 2023/0042173 A1    Feb. 9, 2023

(30) Foreign Application Priority Data
Nov. 18, 2019    (JP) ................................. 2019-208236

(51) Int. Cl.
| | |
|---|---|
| *C12N 15/80* | (2006.01) |
| *C07K 14/37* | (2006.01) |
| *C12N 9/42* | (2006.01) |
| *C12R 1/885* | (2006.01) |

(52) U.S. Cl.
CPC .............. *C12N 15/80* (2013.01); *C07K 14/37* (2013.01); *C12N 9/2437* (2013.01); *C12R 2001/885* (2021.05)

(58) Field of Classification Search
CPC ...... C12N 15/80; C12N 9/2437; C07K 14/37; C12R 2001/885; C12P 21/02
See application file for complete search history.

(56) References Cited

U.S. PATENT DOCUMENTS

| | | | |
|---|---|---|---|
| 6,326,477 B1 | 12/2001 | Ilmén et al. | |
| 9,512,415 B2 | 12/2016 | Pakula et al. | |
| 10,876,103 B2 * | 12/2020 | Ward ..................... | C07K 14/37 |
| 2014/0121446 A1 | 5/2014 | Phillips et al. | |
| 2014/0302587 A1 | 10/2014 | Ben Chaabane et al. | |
| 2019/0309276 A1 | 10/2019 | Ward et al. | |

FOREIGN PATENT DOCUMENTS

| | | |
|---|---|---|
| CN | 103436542 A | 12/2013 |
| CN | 105802854 A | 7/2016 |
| CN | 106978360 A | 7/2017 |
| CN | 108795988 A | 11/2018 |
| JP | H11-512930 A | 11/1999 |
| JP | 5366286 B | 9/2013 |
| JP | 2015-039349 A | 3/2015 |
| JP | 6169077 B | 7/2017 |
| JP | 2019-528797 A | 10/2019 |
| JP | 2022-161526 A | 10/2022 |
| WO | WO 2004/035070 A1 | 4/2014 |
| WO | WO 2017/177289 A1 | 10/2017 |
| WO | WO 2018/067599 A1 | 4/2018 |

OTHER PUBLICATIONS

Derntl et al., Mutation of the Xylanase regulator 1 causes a glucose blind hydrolase expressing phenotype in industrially used Trichoderma strains. Biotechnol. Biofuels., 2013, vol. 6:62, pp. 1-11 (Year: 2013).*

International Search Report for PCT/JP2020/042489; I.A. fd Nov. 13, 2020) mailed Jan. 19, 2021, the Japan Patent Office, Tokyo, Japan.

International Preliminary Report on Patentability (IPRP), Chapter I of the Patent Cooperation Treaty, including the Written Opinion, for PCT/JP2020/042489; I.A. fd Nov. 13, 2020), issued May 17, 2022, by the International Bureau of WIPO, Geneva, Switzerland.

Ilmén M, et al., "Regulation of cellulase gene expression in the filamentous fungus *Trichoderma reesei*," Appl Environ Microbiol. Apr. 1997;63(4):1298-306. doi: 10.1128/aem.63.4.1298-1306.1997. PMID: 9097427; PMCID: PMC168424.

Amore A, et al., "Regulation of cellulase and hemicellulase gene expression in fungi," Curr Genomics. Jun. 2013;14(4):230-49. doi: 10.2174/1389202911314040002. PMID: 24294104; PMCID: PMC3731814.

Lichius A, et al., "Genome sequencing of the *Trichoderma reesei* QM9136 mutant identifies a truncation of the transcriptional regulator XYR1 as the cause for its cellulase-negative phenotype," BMC Genomics. Apr. 20, 2015;16(1):326 (20 pages). doi: 10.1186/s12864-015-1526-0.

Lichius A, et al., Erratum to: "Genome sequencing of the *Trichoderma reesei* QM9136 mutant identifies a truncation of the transcriptional regulator XYR1 as the cause for its cellulase-negative phenotype," (originally published at BMC Genomics. Apr. 20, 2015;16(1):326. doi: 10.1186/s12864-015-1526-0.) Erratum published Sep. 22, 2015 at: BMC Genomics. 2015;16(1): 725, (1 page), PMID: 25909478; PMCID: PMC4409711.

(Continued)

*Primary Examiner* — Ganapathirama Raghu
(74) *Attorney, Agent, or Firm* — Sterne, Kessler, Goldstein & Fox P.L.L.C.

(57) ABSTRACT

A method for producing a mutant filamentous fungus. The method comprises modifications of XYR1 and ACE3 expression in the parent filamentous fungus. The modification of XYR1 is substitution, deletion, insertion, or addition of at least one amino acid residue in a region corresponding to positions 810 to 833 of SEQ ID NO: 1 in a polypeptide that consists of the amino acid sequence of SEQ ID NO: 1 or an amino acid sequence having at least 90, identity thereto and functions as a transcriptional activator of cellulase and hemicellulase, and the modification of ACE3 expression is enhanced expression of a partial polypeptide of ACE3.

20 Claims, 4 Drawing Sheets

Specification includes a Sequence Listing.

(56)                    References Cited

OTHER PUBLICATIONS

Derntl C, et al., Mutation of the Xylanase regulator 1 causes a glucose blind hydrolase expressing phenotype in industrially used *Trichoderma strains*. Biotechnol Biofuels 6:62 (May 2, 2013; 11 pages). https://doi.org/10.1186/1754-6834-6-62.

Ellilä S, et al., "Development of a low-cost cellulase production process using *Trichoderma reesei* for Brazilian biorefineries," Biotechnol Biofuels 10:30 (Feb. 2, 2017; 17 pages). https://doi.org/10.1186/s13068-017-0717-0.

NCBI Reference Sequence: XP_006966092.1, xylanase regulator 1 [Trichodema reesei QM6a], PLN Feb. 5, 2020, version XP_006966092.1, downloaded Jul. 26, 2022 from https://www.ncbi.nlm.nih.gov/protein/XP_006966092.1/.

Fonseca L, et al., "Rational engineering of the *Trichoderma reesei* RUT-C30 strain into an industrially relevant platform for cellulase production," Biotechnol Biofuels 13:93 (May 22, 2020; 15 pages). https://doi.org/10.1186/s13068-020-01732-w.

Zhang J, et al., "The transcription factor ACE3 controls cellulase activities and lactose metabolism via two additional regulators in the fungus *Trichoderma reesei*," J Biol Chem. Nov. 29, 2019;294(48):18435-18450. doi: 10.1074/jbc.RA119.008497. Epub Sep. 9, 2019. PMID: 31501242; PMCID: PMC6885621.

Luo Y, et al., "Modification of transcriptional factor ACE3 enhances protein production in *Trichoderma reesei* in the absence of cellulase gene inducer," Biotechnol Biofuels 13:137 (Aug. 6, 2020; 16 pages). https://doi.org/10.1186/s13068-020-01778-w.

Fei Zhang et al., "Induction and regulation of cellulase expression in filamentous fungi: a review," Chin J. Biotech, 2016, 32(11): 1481-1495 (14 pages).

Hasper AA et al., "Functional analysis of the transcriptional activator XlnR from Aspergillus niger." Microbiology (Reading). May 2004; 150(Pt 5):1367-1375. doi: 10.1099/mic.0.26557-0.

* cited by examiner

MUTANT FILAMENTOUS FUNGUS, AND METHOD FOR PRODUCING PROTEIN USING SAME

FIELD OF THE INVENTION

The present invention relates to a mutant filamentous fungus and a method for producing a protein using the fungus.

BACKGROUND OF THE INVENTION

Filamentous fungi produce various types of cellulases and hemicellulases and are therefore attracting attention as a degrading microorganism of plant polysaccharides. In particular, Trichoderma can produce cellulase and hemicellulase simultaneously and in large quantities and is therefore attracting attention as a microorganism for producing cellulase-based biomass-degrading enzymes.

It is desirable that the carbon source for industrial culture of microorganisms is inexpensive and soluble. Conventionally, glucose has been used widely as a carbon source in the culture of microorganisms. However, in the presence of glucose, a decrease or saturation in the substance productivity of a microorganism is caused by a regulatory mechanism called catabolite repression. It has been reported that wide-range regulatory transcription factors CreA, CreB, CreC, and CreD, are involved in the catabolite repression of filamentous fungi such as Aspergillus (Patent Literature 1). Although there is a possibility that the catabolite repression of Aspergillus can be modulated by controlling these transcription factors, not enough results have been obtained yet. Also regarding Trichoderma, the analysis of the mechanism of catabolite repression is in progress (Patent Literature 2, Non Patent Literature 1). However, there are still many unclear points in the mechanism of the catabolite repression of Trichoderma, and it has not reached the avoidance of the repression.

In production of a protein, such as an enzyme, by a microorganism, an inducer may be needed. For example, in Trichoderma, expression of main cellulase genes cbh1, cbh2, egl1, and egl2 is induced by cellulose, cellobiose, etc., and an inducer is indispensable in cellulase production (Non Patent Literature 2). In general, for example, Avicel, which is microcrystalline cellulose, is used as the inducer in cellulase production. However, the cellulose substrates are expensive, and many of them are insoluble and apply a load to the industrial process. Consequently, the use for industrial purposes is difficult in terms of cost and facilities.

A cellulase-producing method using soluble lactose as an inducer without using cellulose (Patent Literature 3) and a method for synthesizing a saccharide having inductivity of sophorose, gentiobiose, etc. from glucose by reacting cellulase (including 0-glucosidase, endoglucanase, and cellobiohydrolase) derived from Trichoderma and glucose at high temperature (Patent Literature 4) have been disclosed. However, the cellulase production using a saccharide having inductivity also has disadvantages in terms of cost and process load.

Analysis of the cellulase expression mechanism is in progress toward the production of a microorganism that can express cellulase and xylanase without using an inducer by modification of the transcriptional regulator. Previously reported positive transcription factors involved in cellulase inducible expression of Trichoderma include XYR1, ACE2, ACE3, and HAP2/3/5 (Non Patent Literature 3). It has been reported that the cellulase productivity of Trichoderma is lost by shortening 140 amino acids on the C-terminal of XYR1 and that Trichoderma having A824V mutation in XYR1 has deregulation of xylanase to increase the cellulase production (Non Patent Literatures 3 and 4). Non Patent Literature 5 reports that in a Trichoderma strain, protein productivity in a medium containing glucose or sucrose as a carbon source is improved by combining V821F mutation in XYR1 with improved expression of ACE2. Incidentally, since it has been inferred that the gene sequence of XYR1 includes an intron of 20 amino acids region upstream the coding region of the fungal-specific transcription factor domain (Non Patent Literature 6), A824 and V821 of XYR1 disclosed in the above-mentioned literatures were temporarily corrected to A804 and V801, respectively. However, on the other hand, it has also been reported before that the 20 amino acids region is not an intron and is translated into amino acids. Recently, the latter finding is believed to be correct (e.g., Non Patent Literatures 5 and 7). In such the case, it is recognized that A824 and V821 disclosed in the above-mentioned literatures indicate correct amino acid numbers in the sequence of XYR1.

Non Patent Literature 8 suggests that the interaction between ACE3 and XYR1 regulates the cellulase gene expression of Trichoderma reesei. Patent Literature 5 discloses a method for increasing or decreasing the productivity of cellulase or the like in Trichoderma reesei by increasing or decreasing the expression of the tre77513 (ACE3) gene. Patent Literature 6 and Non Patent Literature 9 report that a filamentous fungus showing improved expression of modified ACE3, in which all six cysteines of the $Zn(II)_2Cys_6$-type DNA-binding domain on the N-terminal are maintained and the amino acids on the C-terminal are deleted, showed improved expression of cellulase even in the absence of an inducer.

Furthermore, Non Patent Literature 9 describes a filamentous fungus that shows improved expression of the C-terminal deleted ACE3 and further shows co-expression with the wild-type or A824V mutant of XYR1. However, the effect on the cellulase expression by the co-expression of the XYR1 in this filamentous fungus is slightly observed in the presence of an inducer, but is not observed in the absence of an inducer.

(Patent Literature 1) JP-A-2015-39349
(Patent Literature 2) JP-A-11-512930
(Patent Literature 3) Japanese Patent No. 6169077
(Patent Literature 4) Japanese Patent No. 5366286
(Patent Literature 5) U.S. Pat. No. 9,512,415
(Patent Literature 6) WO 2018/067599
(Non Patent Literature 1) Appl. Environ. Microbiol., 1997, 63:1298-1306
(Non Patent Literature 2) Curr. Genomics, 2013, 14:230-249
(Non Patent Literature 3) BMC Genomics, 2015, 16:326
(Non Patent Literature 4) Biotech. Biofuels, 2013, 6:62
(Non Patent Literature 5) Biotech. Biofuels, 2017, 10:30
(Non Patent Literature 6) NCBI Reference Sequence: XP_006966092.1 [www.ncbi.nlm.nih.gov/protein/XP_006966092.1]
(Non Patent Literature 7) Biotech. Biofuels, 2020, 13:93
(Non Patent Literature 8) J. Biol. Chem., 2019, doi:10.1074/jbc.RA119.008497
(Non Patent Literature 9) Biotech. Biofuels, 2020, 13:137

SUMMARY OF THE INVENTION

The present invention provides a method for producing a mutant filamentous fungus, the method comprising:

modifying XYR1 and ACE3 expression in a parent fila-
mentous fungus, wherein
the modification of XYR1 is substitution, deletion, inser-
tion, or addition of at least one amino acid residue in a
region corresponding to positions 810 to 833 of SEQ
ID NO: 1 in a polypeptide that consists of the amino
acid sequence of SEQ ID NO: 1 or an amino acid
sequence having at least 90, identity thereto and func-
tions as a transcriptional activator of cellulase and
hemicellulase, and
the modification of ACE3 expression is enhanced expres-
sion of a polypeptide that consists of the amino acid
sequence at positions 107 to 734 of SEQ ID NO: 3 or
an amino acid sequence having at least 90% identity
thereto.

DETAILED DESCRIPTION OF THE INVENTION

Figure 1:
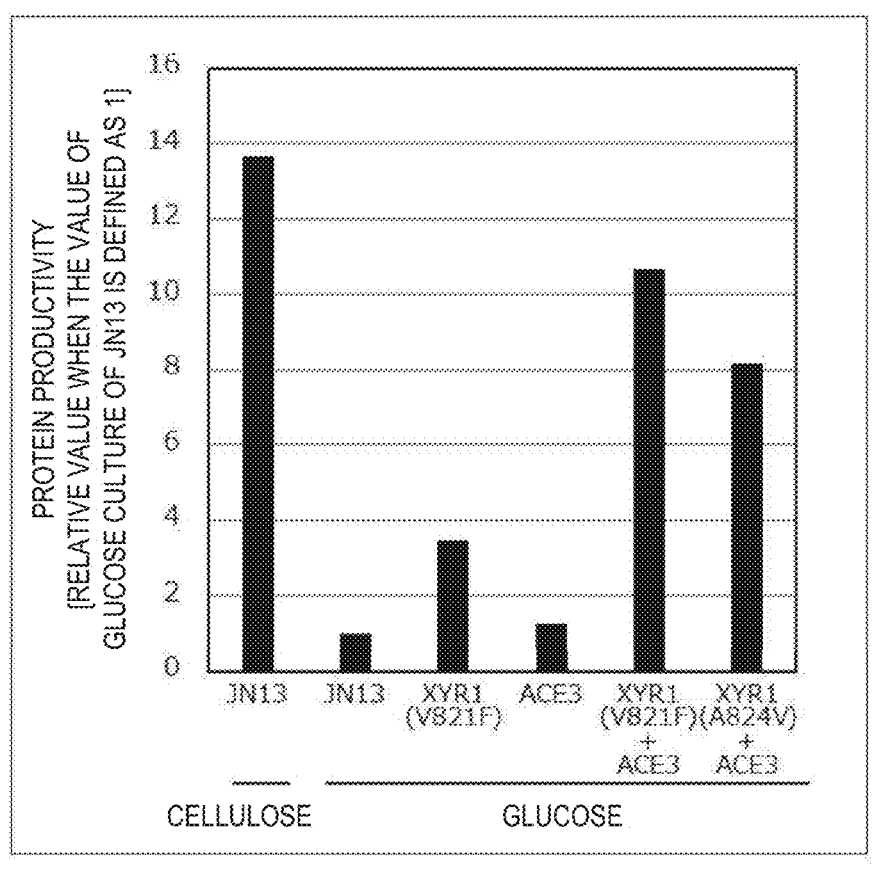
FIG. 1 shows relative protein productivity of mutant
filamentous fungus strains.

All Patent Literatures, Non Patent Literatures, and other
publications cited herein are hereby incorporated by refer-
ence in their entirety.

The identity in an amino acid sequence or a nucleotide
sequence as described herein is calculated by a Lipman-
Pearson method (Science, 1985, 227:1435-1441). Specifi-
cally, the identity is calculated by performing analysis using
the homology analysis (Search homology) program of
genetic information processing software Genetyx-Win (Ver.
5.1.1, Software Development Co., Ltd.) and setting the Unit
size to compare (ktup) to 2.

As used herein, the term "at least 90% identity" in the
context of an amino acid sequence and a nucleotide
sequence refers to an identity of 90% or more, preferably
92% or more, more preferably 94% or more, further pref-
erably 95% or more, further preferably 96% or more, further
preferably 98% or more, and still preferably 991 or more.

As used herein, the term "one to several" that is used in
the context of deletion, substitution, addition, or insertion of
amino acid or nucleotide in an amino acid sequence or a
nucleotide sequence can mean, for example, from 1 to 20,
preferably from 1 to 16, more preferably from 1 to 12,
further preferably from 1 to 8, and further preferably from
1 to 4, unless otherwise defined. As used herein, the "addi-
tion" of amino acid or nucleotide includes addition of one to
several amino acids or nucleotides to one end and both ends
of a sequence. As used herein, the "insertion" of amino acid
or nucleotide includes insertion of amino acid or nucleotide
into the 5' side or the 3' side of a predetermined position.

As used herein, the "corresponding position" or "corre-
sponding region" in an amino acid sequence or a nucleotide
sequence can be determined by aligning (alignment of) a
target sequence and a reference sequence (for example, the
amino acid sequence of SEQ ID NO: 1) so as to give a
maximum homology. The alignment of an amino acid
sequence or nucleotide sequence can be performed using a known algorithm, and the procedure thereof is known to
those skilled in the art. For example, the alignment can be
performed using the Clustal W Multiple Alignment program
(Thompson, J. D. et al, 1994, Nucleic Acids Res. 22:4673-
4680) at the default setting. The Clustal W can be used on
the website of, for example, the European Bioinformatics
Institute: EBI [www.ebi.ac.uk/index.html] or the DNA Data
Bank of Japan (DDBJ [www.ddbj.nig.ac.jp/searches-
j.html]) managed by the National Institute of Genetics. The
position of a target sequence aligned to an arbitrary position
of a reference sequence by the above-mentioned alignment
is regarded as the "position corresponding" to the arbitrary
position. A region between corresponding positions or a
region consisting of a corresponding motif is regarded as a
corresponding region.

Those skilled in the art can further finely adjust the
alignment of an amino acid sequence obtained above to
optimize it. Such optimized alignment is preferably deter-
mined by considering, for example, the similarity of amino
acid sequences and the frequency of insertion of a gap. Here,
the similarity of amino acid sequences refers to, when two
amino acid sequences are aligned, the proportion (%) of the
number of positions at which the same or analogous amino
acid residue is present in both aligned sequences relative to
the number of full-length amino acid residues. The analo-
gous amino acid residues are amino acid residues having
similar properties to each other in polarity and charge, more
specifically, capable of causing conservative substitution,
among the 20 amino acid residues constituting proteins. The
groups consisting of such similar amino acid residues are
well known to those skilled in the art, and examples thereof
include, but not limited to, arginine and lysine; glutamic acid
and aspartic acid; serine and threonine; glutamine and
asparagine; and leucine and isoleucine.

As used herein, the term "amino acid residue" means 20
amino acid residues constituting proteins, i.e., alanine (Ala
or A), arginine (Arg or R), asparagine (Asn or N), aspartic
acid (Asp or D), cysteine (Cys or C), glutamine (Gln or Q),
glutamic acid (Glu or E), glycine (Gly or G), histidine (His
or H), isoleucine (Ile or I), leucine (Leu or L), lysine (Lys or
K), methionine (Met or M), phenylalanine (Phe or F),
proline (Pro or P), serine (Ser or S), threonine (Thr or T),
tryptophan (Trp or W), tyrosine (Tyr or Y), and valine (Val
or V).

As used herein, the term "operable linkage" between a
control region, such as a promoter, and a gene means that the
gene and the control region are linked to each other such that
the gene can be expressed under the control of the control
region. The procedure of the "operable linkage" between a
gene and a control region is known to those skilled in the art.

As used herein, "upstream" and "downstream" in the
context of a gene refer to upstream and downstream in the
transcription direction of the gene. For example, "a gene
located downstream of a promoter" means that the gene is
present on the 3' side of the promoter in the DNA sense
strand, and upstream of a gene means the region on the 5'
side of the gene in the DNA sense strand.

As used herein, the term "intrinsic" used for function,
property, and trait of a cell is used for representing that the
function, property, and trait are originally present in the cell.
In contrast, the term "exogenous" is used for representing
that the function, property, and trait are not originally present
in the cell but exogenously introduced. For example, an
"exogenous" gene or polynucleotide is a gene or polynucle-
otide introduced into a cell from the outside. The exogenous
gene or polynucleotide may be derived from an organism of
the same species as the cell into which the gene or polynucleotide has been introduced, or may be derived from an organism of a different species (that is, a heterologous gene or polynucleotide).

The present invention provides a mutant filamentous fungus, a method for producing the fungus, and a method for producing a protein using the mutant filamentous fungus. The present invention relates to improvement in the protein productivity of a filamentous fungus. Conventionally, when a filamentous fungus is cultured in the presence of glucose, the protein productivity is decreased by catabolite repression in some cases. In particular, expression of a cellulase-based biomass-degrading enzyme, such as cellulase and hemicellulase, in a filamentous fungus is necessarily induced by a cellulase inducer such as cellulose, sophorose, and cellooligosaccharide (cellobiose, cellotriose, cellotetraose, cellopentaose, cellohexaose, etc.). In contrast, the expression induction is suppressed in the presence of glucose.

The present inventors found that a mutant filamentous fungus modified by combining XYR1 and ACE3 expression shows an enhanced production of a protein, such as cellulase and hemicellulase, without using an inducer which is indispensable for conventional production of cellulase and hemicellulase. In the present invention, when predetermined modifications are respectively made to XYR1 and ACE3, which are transcriptional activators of cellulase and hemicellulase, of a filamentous fungus, the filamentous fungus is imparted with the ability to express cellulase and hemicellulase without using a cellulase inducer such as cellulose and can highly express a protein, such as cellulase and hemicellulase, in the presence of a cellulase noninducible carbon source, such as glucose. The cellulase and hemicellulase expression capacity is significantly improved by modifying XYR1 and ACE3 expression in combination compared to the case of modifying only one of them. It is inferred that the modifications of XYR1 and ACE3 expression contribute to alleviation of the catabolite repression or transcriptional enhancement of cellulase and hemicellulase.

The filamentous fungus provided by the present invention can efficiently produce a protein even in an environment in which the main carbon source is a cellulase noninducible carbon source such as glucose. The filamentous fungus can efficiently produce a protein, such as cellulase and hemicellulase, even not using an expensive cellulase inducer. According to the present invention, it is possible to increase the efficiency and decrease the cost of protein production using a filamentous fungus.

Accordingly, in an aspect, the present invention provides a mutant filamentous fungus and a method for producing the fungus. Basically, the method for producing a mutant filamentous fungus of the present invention includes modifications of XYR1 and ACE3 expression in a parent filamentous fungus. In the method, the order of the modifications of XYR1 and ACE3 expression is not limited as long as each of the modifications can be achieved.

Examples of the parent filamentous fungus used in the present invention include, but not limited to, filamentous fungi belonging to the division Eumycota or the division Oomycota. More specifically, the examples thereof include filamentous fungi of *Trichoderma, Aspergillus, Penicillium, Neurospora, Fusarium, Chrysosporium, Humicola, Emericella, Hypocrea, Acremonium, Chrysosporium, Myceliophthora, Piromyces, Talaromyces, Thermoascus*, and *Thielavia*. Among these filamentous fungi, filamentous fungi of *Trichoderma* are preferable.

Examples of the filamentous fungi of *Trichoderma* include *Trichoderma reesei, Trichoderma longibrachiatum, Trichoderma harzianum, Trichoderma koningii*, and *Tricho-*

*derma viride*, and preferable examples are *Trichoderma reesei* and its mutant strain. For example, *Trichoderma reesei* QM9414 strain and its mutant strain, preferably *Trichoderma reesei* PC-3-7 strain (ATCC66589), *Trichoderma reesei* PCD-10 strain (FERM P-8172), *Trichoderma reesei* JN13 strain, or a mutant strain thereof, can be preferably used as a parent filamentous fungus.

XYR1 (Xylanase regulator 1) is a transcriptional activator of cellulase and hemicellulase in a filamentous fungus. XYR1 has a $Zn(II)_2Cys_6$ binuclear cluster domain and is a main factor for xylanase gene expression regulation, and is conserved widely in Ascomycetes excluding yeasts, such as *Trichoderma* (XYR1), *Fusarium* (XYR1), *Neurospora* (XYR1), and *Aspergillus* (XLNR). XYR1 of *Trichoderma reesei* manages all of genes for xylanase/xylose metabolism and cellulase genes. The XYR1 of *Trichoderma reesei* has been registered in ncbi database (www.ncbi.nlm.nih.gov/]) as NCBI Reference Sequence: XP_006966092.1.

Conventionally, it has been inferred that the gene sequence of XYR1 includes an intron of a 20 amino acids region upstream (the region from 1024th to 1083rd nucleotides of SEQ ID NO: 2) of the coding region of a fungal-specific transcription factor domain, and it has been inferred that the full-length of XYR1 consists of 920 amino acids. In also the above-mentioned ncbi database (Non Patent Literature 6), XYR1 of XP_006966092.1 consists of the amino acid sequence (SEQ ID NO: 51) of 920 amino acids length and is prescribed as a polypeptide encoded by the nucleotide sequence of SEQ ID NO: 2. On the other hand, it has been conventionally reported that the region from 1024th to 1083rd nucleotides of SEQ ID NO: 2 is not an intron and is translated into amino acids. Recently, it is inferred that the latter is the correct structure of XYR1 (for example, Non Patent Literatures 5 and 7). In such the case, XYR1 has the region from 320th to 339th amino acids encoded by the region from 1024th to 1083rd nucleotides of SEQ ID NO: 2, and the full length thereof is 940 amino acids.

Considering the above circumstances, unless otherwise explained, the amino acid sequence of XYR1 as disclosed herein is represented by SEQ ID NO: 1 of 940 amino acids length, and the number of an amino acid residue of XYR1 (the position on the amino acid sequence) is represented by the number (position) of the residue in the sequence of SEQ ID NO: 1. In addition, considering the above circumstances, amino acid residues after position 340 of SEQ ID NO: 1 as disclosed herein should be interpreted as the amino acid residue at position [(the position of SEQ ID NO: 1)–20] of SEQ ID NO: 51. For example, positions 810 to 833 of SEQ ID NO: 1 are positions 790 to 813 of SEQ ID NO: 51. That is, position 810 of SEQ ID NO: 1 corresponds to position 790 of SEQ ID NO: 51; position 833 of SEQ ID NO: 1 corresponds to position 813 of SEQ ID NO: 51; and positions 821 and 824 of SEQ ID NO: 1 correspond to positions 801 and 804 of SEQ ID NO: 51, respectively. The same applies to other positions.

Accordingly, examples of XYR1 (parent XYR1) to be modified in the present invention include a polypeptide consisting of the amino acid sequence of SEQ ID NO: 1. Other examples of the parent XYR1 include a polypeptide consisting of an amino acid sequence having at least 90% identity to the amino acid sequence of SEQ ID NO: 1 and functioning as a transcriptional activator of cellulase and hemicellulase. Example of the amino acid sequence having at least 90% identity to SEQ ID NO: 1 include an amino acid sequence in which one to several amino acid residues are deleted, substituted, added, or inserted in the amino acid sequence of SEQ ID NO: 1.

The modification of XYR1 in the present invention is addition of a mutation of at least one amino acid residue to a region that is assumed to be an α-helix in the acidic activation domain of parent XYR1. More specifically, the modification of XYR1 is performed by a mutation (i.e., substitution, deletion, insertion, or addition) of at least one amino acid residue in a region corresponding to positions 771 to 865 of SEQ ID NO: 1 in a polypeptide that consists of the amino acid sequence of SEQ ID NO: 1, which is the parent XYR1, or an amino acid sequence having at least 90% identity thereto and functions as a transcriptional activator of cellulase and hemicellulase. In a preferable embodiment, the at least one amino acid residue to be mutated is located in a region corresponding to positions 810 to 833 of SEQ ID NO: 1.

In a preferable embodiment, the above-described at least one amino acid residue is substituted. The amino acid residue to be substituted is at least one selected from the group consisting of Val, Ile, Leu, Ala, Gly, Thr, and Glu; more preferably, at least one selected from the group consisting of the following (1) and (2): (1) Val, Ile, or Leu and (2) Ala or Gly, or at least one selected from the group consisting of Val, Ala, Thr, and Glu; and further preferably, at least one selected from the group consisting of Val and Ala. Preferably, these amino acid residues are each substituted with Val, Glu, Ile, Leu, Lys, Phe, Thr, Trp, or Tyr.

Preferable examples of the substitution of Val, Ile, Leu, Ala, Gly, Thr, or Glu include the followings:

substitution of Val with Lys, Phe, Trp, or Tyr;

substitution of Ile with Phe, Trp, or Tyr;

substitution of Leu with Phe, Trp, or Tyr;

substitution of Ala with Val, Glu, Ile, Leu, Lys, Phe, Thr, Trp, or Tyr;

substitution of Gly with Val, Ile, Leu, Phe, Trp, or Tyr;

substitution of Thr with Tyr; and substitution of Glu with Tyr.

In a more preferable embodiment, the substitution of an amino acid residue is at least one selected from the group consisting of the followings:

substitution of Gly at the position corresponding to position 812 of SEQ ID NO: 1 with Val, Ile, Leu, Phe, Trp, or Tyr;

substitution of Val at the position corresponding to position 814 of SEQ ID NO: 1 with Phe, Trp, or Tyr;

substitution of Ala at the position corresponding to position 816 of SEQ ID NO: 1 with Val, Ile, Leu, Phe, Trp, or Tyr;

substitution of Thr at the position corresponding to position 817 of SEQ ID NO: 1 with Tyr;

substitution of Ala at the position corresponding to position 820 of SEQ ID NO: 1 with Val, Ile, Leu, Phe, Trp, or Tyr;

substitution of Val at the position corresponding to position 821 of SEQ ID NO: 1 with Lys, Phe, Trp, or Tyr;

substitution of Ala at the position corresponding to position 823 of SEQ ID NO: 1 with Val, Ile, Leu, Phe, Trp, or Tyr;

substitution of Ala at the position corresponding to position 824 of SEQ ID NO: 1 with Val, Glu, Ile, Leu, Lys, Phe, Thr, Trp, or Tyr;

substitution of Glu at the position corresponding to position 825 of SEQ ID NO: 1 with Tyr;

substitution of Ala at the position corresponding to position 826 of SEQ ID NO: 1 with Val, Ile, Leu, Phe, Trp, or Tyr;

substitution of Ile at the position corresponding to position 827 of SEQ ID NO: 1 with Phe, Trp, or Tyr;

substitution of Ile at the position corresponding to position 830 of SEQ ID NO: 1 with Phe, Trp, or Tyr; and substitution of Leu at the position corresponding to position 831 of SEQ ID NO: 1 with Phe, Trp, or Tyr.

In a further preferable embodiment, the modification of XYR1 according to the present invention is performed for the parent XYR1 by substitution of an amino acid residue at at least one position selected from the group consisting of the positions corresponding to positions 817, 821, 824, 825, and 826 of SEQ ID NO: 1. The amino acid residues substituting for the positions corresponding to positions 817, 821, 824, 825, and 826 are, respectively, as described above.

In another further preferable embodiment, the modification of XYR1 according to the present invention is performed for the parent XYR1 by substitution of an amino acid residue at at least one position selected from the group consisting of the positions corresponding to positions 821 and 824 of SEQ ID NO: 1. The amino acid residue substituting for the position corresponding to position 821 is preferably Lys, Phe, Trp, or Tyr, more preferably Phe, and further preferably Lys or Tyr. The amino acid residue substituting for the position corresponding to position 824 is preferably Val, Glu, Ile, Leu, Lys, Phe, Thr, Trp, or Tyr, more preferably Val, and further preferably Glu, Ile, Leu, Lys, Phe, Thr, Trp, or Tyr.

In another further preferable embodiment, the modification of XYR1 according to the present invention is performed for the parent XYR1 by substitution of an amino acid residue at at least one position selected from the group consisting of the positions corresponding to positions 817, 825, and 826 of SEQ ID NO: 1. The amino acid residue substituting for the position corresponding to position 817 is preferably Tyr. The amino acid residue substituting for the position corresponding to position 825 is preferably Tyr. The amino acid residue substituting for the position corresponding to position 826 is preferably Val, Ile, Leu, Phe, Trp, or Tyr and more preferably Val or Trp.

In one example, the amino acid residues at the positions corresponding to positions 817, 821, 824, 825, and 826 of SEQ ID NO: 1 in the parent XYR1 are, respectively, not the amino acid residues after the substitutions above. Preferably, the amino acid residues at the positions corresponding to positions 817, 821, 824, 825, and 826 of SEQ ID NO: 1 in the parent XYR1 are, respectively, the same as the amino acid residues at positions 817, 821, 824, 825, and 826 of SEQ ID NO: 1.

In another example, the amino acid residues at the positions corresponding to positions 812, 814, 816, 817, 820, 821, 823, 824, 825, 826, 827, 830, and 831 of SEQ ID NO: 1 in the parent XYR1 are, respectively, not the amino acid residues after the substitutions above. Preferably, the amino acid residues at the positions corresponding to positions 812, 814, 816, 817, 820, 821, 823, 824, 825, 826, 827, 830, and 831 of SEQ ID NO: 1 in the parent XYR1 are, respectively, the same as the amino acid residues at positions 812, 814, 816, 817, 820, 821, 823, 824, 825, 826, 827, 830, and 831 of SEQ ID NO: 1.

In another example, the amino acid sequence of a region corresponding to positions 810 to 833 of SEQ ID NO: 1 in the parent XYR1 is the same as the sequence at positions 810 to 833 of SEQ ID NO: 1.

As the method for introducing mutation (substitution, deletion, insertion, or addition) into an amino acid residue of the polypeptide of a parent filamentous fungus, various mutation methods that are known in the art can be used. For example, in the genome of a parent filamentous fungus, the polynucleotide (hereinafter, also referred to as parent gene)

coding for the amino acid sequence (parent XYR1) to be mutated is changed to a polynucleotide (hereinafter, also referred to as mutated gene) coding for a mutated amino acid sequence, and a polypeptide (modified XYR1) including the target mutation can be expressed from the mutated gene.

Examples of the method for introducing a target mutation into a parent gene include a method using homologous recombination. For example, a parent gene in the genome of a parent filamentous fungus can be substituted with a mutant gene by homologous recombination. In an example of a specific method of the homologous recombination, first, a DNA construct for homologous recombination including a mutated gene and as needed, a drug-resistant gene or auxotrophic gene is constructed, and is introduced into a parent filamentous fungus by a common method. Secondly, a transformant in which the construct for homologous recombination is incorporated on the genome is selected using, for example, the drug resistance or auxotrophy as an index. As needed, it may be confirmed that the resulting transformant includes a target mutation by genomic analysis or enzyme activity analysis.

The DNA construct for homologous recombination can be constructed by introducing a site-specific mutation into an isolated parent gene. The site-specific mutation introduction can be performed by a common method in the art, such as an inverse PCR method, an annealing method, or an SOE (splicing by overlap extension)-PCR (Gene, 1989, 77(1):p 61-68). A commercially available site-specific mutation introduction kit (for example, QuickChange II Site-Directed Mutagenesis Kit and QuickChange Multi Site-Directed Mutagenesis Kit of Stratagene) may be used.

In the introduction of the DNA construct into the parent filamentous fungus, a vector that is generally used in transformation of a plasmid or the like can be used. In the introduction of the DNA construct or the vector into a cell, for example, a common method, such as a protoplast method, a protoplast PEG method, or a competent cell method, can be used.

The parent gene can be isolated by a common method from, for example, a filamentous fungus strain that is the same species as the parent filamentous fungus. Alternatively, the parent gene may be chemically synthesized based on the nucleotide sequence of the parent gene. As needed, the parent gene may be codon-optimized for the host (parent filamentous fungus) into which the gene is introduced. The information on codons that are used by various organisms is available from Codon Usage Database ([www.kazusa.or.jp/codon/]).

The parent gene may be any polynucleotide that codes for the above-described parent XYR1, i.e., a polypeptide that consists of the amino acid sequence of SEQ ID NO: 1 or an amino acid sequence having at least 90% identity thereto and functions as a transcriptional activator of cellulase and hemicellulase. Examples of such the polynucleotide include a polynucleotide consisting of the nucleotide sequence of SEQ ID NO: 2 or a nucleotide sequence having at least 90% identity thereto.

The introduction of a site-specific mutation to the parent gene can be performed most generally using a mutation primer including a nucleotide mutation to be introduced. The mutation primer may be annealed to a region including a sequence coding for the amino acid residue to be mutated in the parent gene and may be designed so as to include a sequence (codon) coding for the amino acid residue after the mutation instead of the sequence (codon) coding for the amino acid residue to be mutated. The sequences (codons) coding for the amino acid residues before and after the mutation can be appropriately perceived and selected based on a usual textbook by those skilled in the art. Alternatively, the site-specific mutation introduction can be performed by linking DNA fragments upstream and downstream a target region including a nucleotide mutation to be introduced and amplified respectively using 2 sets of primers, into one by SOE-PCR. The mutation primer can be produced by a well-known oligonucleotide synthesis method, such as a phosphoramidite method (Nucleic Acids Research, 1989, 17:7059-7071).

Alternatively, the parent filamentous fungus is subjected to mutation treatment, and a strain including a target mutation can be subsequently selected by genomic analysis or enzyme activity analysis. Examples of the mutation treatment include the use of N-methyl-N'-nitro-N-nitrosoguanidine (NTG) or ethylnitrosourea, or irradiation of ultraviolet rays or radioactive rays. Various alkylating agents and carcinogens can also be used as mutagens.

The modification of ACE3 expression according to the present invention is enhancement of the expression of ACE3 or its partial polypeptide. ACE3 is a transcriptional activator of cellulase and hemicellulase in a filamentous fungus. ACE3 is indispensable for transcription of the cellulase gene during lactose induction and of a part of xylanase genes. ACE3 is also partially involved in transcriptional regulation of xyr1. ACE3 of *Trichoderma reesei* has been registered in ncbi database (www.ncbi.nlm.nih.gov/]) as NCBI Reference Sequence: QEM24913.1. Here, ACE3 is prescribed as a polypeptide that consists of the amino acid sequence of SEQ ID NO: 3 and is encoded by the nucleotide sequence of SEQ ID NO: 4. According to Non Patent Literature 6, the region at positions 523 to 734 in the amino acid sequence of SEQ ID NO: 3 is assumed to interact with XYR1, the region at positions 391 to 522 is assumed to be a filamentous fungus-specific transcription factor domain, and the region at positions 120 to 160 is assumed to be a $Zn(II)_2Cys_6$-type DNA-binding domain.

Accordingly, examples of ACE3 or its partial polypeptides to be enhanced in expression in the present invention include a polypeptide consisting of the amino acid sequence of SEQ ID NO: 3 or its partial polypeptide. Other examples of ACE3 or its partial polypeptides include a polypeptide consisting of an amino acid sequence having at least 90% identity to the amino acid sequence of SEQ ID NO: 3 and functioning as a transcriptional activator of cellulase and hemicellulase, or its partial polypeptide. Examples of the amino acid sequence having at least 90, identity to SEQ ID NO: 3 include an amino acid sequence in which one to several amino acid residues are deleted, substituted, added, or inserted in the amino acid sequence of SEQ ID NO: 3.

In the present invention, although expression of the full-length polypeptide of the ACE3 may be enhanced, expression of its partial polypeptide, preferably, a polypeptide at least including a region corresponding to positions 107 to 734 of SEQ ID NO: 3 may be enhanced. Accordingly, examples of the ACE3 to be enhanced in expression in the present invention include a polypeptide consisting of the amino acid sequence at positions 1 to 734 of SEQ ID NO: 3 or an amino acid sequence having at least 90, identity thereto. Examples of the partial polypeptide of ACE3 include a polypeptide consisting of the amino acid sequence at positions 107 to 734 of SEQ ID NO: 3 or an amino acid sequence having at least 90% identity thereto.

ACE3 or its partial polypeptide that is enhanced in expression in the present invention preferably preserves all the 7th to 10th amino acid residues from the C-terminal of wild-type ACE3 (amino acid residues in a region corresponding to positions 725 to 728 of SEQ ID NO: 3). More preferably, ACE3 or its partial polypeptide that is enhanced in expression in the present invention preserves all the 7th to 17th amino acid residues from the C-terminal of wild-type ACE3 (amino acid residues in a region corresponding to positions 718 to 728 of SEQ ID NO: 3). Alternatively, ACE3 or its partial polypeptide that is enhanced in expression in the present invention preferably preserves a region corresponding to 11 amino acids (positions 724 to 734 of SEQ ID NO: 3) at the C-terminal of wild-type ACE3. However, as long as the function as a transcriptional activator of cellulase and hemicellulase can be maintained, mutation of a part of the amino acid residues in a region corresponding to positions 724 to 734 of SEQ ID NO: 3 in the ACE3 or its partial polypeptide (for example, substitution, deletion, insertion, or addition of one or more residues at positions 729 to 734 of SEQ ID NO: 3) is acceptable.

Enhanced expression of ACE3 or its partial polypeptide in the present invention preferably refers to improvement in expression level of the ACE3 or its partial polypeptide. Examples of the method for increasing the expression level of a target polypeptide include a method for improving the transcription level of a gene coding for the polypeptide (hereinafter, also referred to a target gene). Examples of the method for improving the transcription level of a target gene include a method in which a control region (strong control region) that strongly enhances the transcription of a target gene is substituted for or inserted into the control region of the gene on the genome of a parent filamentous fungus to operably link the strong control region to the target gene. Alternatively, the transcription level of a target gene can be improved by introducing a target gene fragment operably linked to a control region (preferably, strong control region) as needed into the genome or plasmid of a parent filamentous fungus to increase the number of the target genes that can be expressed in cells.

Examples of the control region that can be used for improving the transcription level include genes that do not decrease the transcription level even under high glucose conditions, for example, in *Trichoderma* filamentous fungi, control regions of genes, such as glyceraldehyde-3-phosphate dehydrogenase (gpd), pyruvate decarboxylase (pdc), enolase (eno), alcohol dehydrogenase (adh), triose phosphate isomerase (tpi), aldolase (fba), pyruvate kinase (pyk), citrate synthase (cit), α-ketoglutarate dehydrogenase (kdh), aldehyde dehydrogenase I (ald1), aldehyde dehydrogenase II (ald2), pyruvate dehydrogenase (pda), glucokinase (glk), actin (act1), and translation elongation factor 1α (tef1). Among them, preferable examples of the high control region include control regions, such as pdc (TRIREDRAFT 121534) and act1 (TRIREDRAFT 44504).

The target gene can be isolated from, for example, a filamentous fungus strain that is the same species as the parent filamentous fungus by a common method. Alternatively, the target gene may be chemically synthesized based on the nucleotide sequence of the gene of the parent filamentous fungus. Preferable examples of the target gene include a polynucleotide consisting of the nucleotide sequence of SEQ ID NO: 4, a polynucleotide consisting of a nucleotide sequence having at least 901 identity to SEQ ID NO: 4 and coding for a polypeptide that functions as a transcriptional activator of cellulase and hemicellulase, and a partial polynucleotide thereof. Examples of the nucleotide sequence having at least 90% identity to SEQ ID NO: 4 include a nucleotide sequence in which one to several nucleotides are deleted, substituted, added, or inserted in the sequence of SEQ ID NO: 4. Preferable examples of the partial polynucleotide include a polynucleotide coding for the above-described partial polypeptide of ACE3.

The expression level of ACE3 or its partial polypeptide in the mutant strain of the present invention is improved compared to that in the parent filamentous fungus. Alternatively, the transcription level of a gene coding for ACE3 or its partial polypeptide in the mutant strain of the present invention is improved compared to that in the parent filamentous fungus. The expression level of the gene or polypeptide can be quantitatively measured by a known method, such as quantitative PCR, microarray analysis, western blotting, ELISA, or HPLC.

The mutant filamentous fungus of the present invention produced by the above procedure includes modified XYR1 obtained by the above-described modification of XYR1 and shows enhanced expression of ACE3 or its partial polypeptide compared to the parent filamentous fungus as described above.

Examples the ACE3 or its partial polypeptide that shows enhanced expression in the mutant filamentous fungus of the present invention are as described above. Preferably, the mutant filamentous fungus of the present invention has been introduced with a gene coding for a partial polypeptide of ACE3 (preferably a polypeptide consisting of the amino acid sequence at positions 107 to 734 of SEQ ID NO: 3 or an amino acid sequence having at least 90% identity thereto) operably linked to a control region (preferable a strong control region), and thereby the expression of the partial polypeptide of ACE3 is enhanced.

Preferably, the modified XYR1 included in the mutant filamentous fungus of the present invention is a polypeptide having a substitution, deletion, insertion, or addition of at least one amino acid residue in a region corresponding to positions 771 to 865, preferably in a region corresponding to positions 810 to 833, of SEQ ID NO: 1 in the amino acid sequence of SEQ ID NO:1 or an amino acid sequence having at least 90% identity thereto, and functions as a transcriptional activator of cellulase and hemicellulase.

More preferably, the modified XYR1 included in the mutant filamentous fungus of the present invention is a polypeptide having a substitution, deletion, insertion, or addition of at least one amino acid residue in a region corresponding to positions 771 to 865, preferably in a region corresponding to positions 810 to 833, of SEQ ID NO: 1 in the amino acid sequence of SEQ ID NO:1 or an amino acid sequence having at least 90% identity thereto, the substitution being selected from the group consisting of the followings:

substitution of Val with Lys, Phe, Trp, or Tyr;

substitution of Ile with Phe, Trp, or Tyr;

substitution of Leu with Phe, Trp, or Tyr;

substitution of Ala with Glu, Ile, Leu, Lys, Phe, Thr, Trp, or Tyr;

substitution of Gly with Val, Ile, Leu, Phe, Trp, or Tyr;

substitution of Thr with Tyr; and substitution of Glu with Tyr, and the polypeptide functions as a transcriptional activator of cellulase and hemicellulase.

Further preferably, the modified XYR1 is a polypeptide that consists of an amino acid sequence having at least 90% identity to SEQ ID NO: 1 including at least one amino acid residue selected from the group consisting of the following (a) to (m):

(a) Val, Ile, Leu, Phe, Trp, or Tyr at a position corresponding to position 812 of SEQ ID NO: 1;

(b) Phe, Trp, or Tyr at a position corresponding to position 814 of SEQ ID NO: 1;

(c) Val, Ile, Leu, Phe, Trp, or Tyr at a position corresponding to position 816 of SEQ ID NO: 1;

(d) Tyr at a position corresponding to position 817 of SEQ ID NO: 1;

(e) Val, Ile, Leu, Phe, Trp, or Tyr at a position corresponding to position 820 of SEQ ID NO: 1;

(f) Lys, Phe, Trp, or Tyr at a position corresponding to position 821 of SEQ ID NO: 1;

(g) Val, Ile, Leu, Phe, Trp, or Tyr at a position corresponding to position 823 of SEQ ID NO: 1;

(h) Val, Glu, Ile, Leu, Lys, Phe, Thr, Trp, or Tyr at a position corresponding to position 824 of SEQ ID NO: 1;

(i) Tyr at a position corresponding to position 825 of SEQ ID NO: 1;

(j) Val, Ile, Leu, Phe, Trp, or Tyr at a position corresponding to position 826 of SEQ ID NO: 1;

(k) Phe, Trp, or Tyr at a position corresponding to position 827 of SEQ ID NO: 1;

(l) Phe, Trp, or Tyr at a position corresponding to position 830 of SEQ ID NO: 1; and (m) Phe, Trp, or Tyr at a position corresponding to position 831 of SEQ ID NO: 1, and the polypeptide functions as a transcriptional activator of cellulase and hemicellulase.

Further preferably, the modified XYR1 includes at least one of the (a), (c), (e), (g), (h), and (j) and/or at least one of the (b), (f), (k), (l), and (m). Further preferably, the modified XYR1 includes at least one of the (c), (e), (g), (h), and (j) and/or at least one of the (b) and (f).

In a further preferable embodiment, the modified XYR1 is a polypeptide that consists of an amino acid sequence having at least 90% identity to SEQ ID NO: 1 including at least one of the (d), (f), (h), (i), and (j) and functions as a transcriptional activator of cellulase and hemicellulase.

In another further preferable embodiment, the modified XYR1 is a polypeptide that consists of an amino acid sequence having at least 90% identity to SEQ ID NO: 1 including at least one amino acid residue selected from the group consisting of the followings:

Lys, Phe, Trp, or Tyr, preferably Phe, and more preferably Lys or Tyr at a position corresponding to position 821 of SEQ ID NO: 1; and Val, Glu, Ile, Leu, Lys, Phe, Thr, Trp, or Tyr, preferably Val, and more preferably Glu, Ile, Leu, Lys, Phe, Thr, Trp, or Tyr at a position corresponding to position 824 of SEQ ID NO: 1, and the polypeptide functions as a transcriptional activator of cellulase and hemicellulase.

In another further preferable embodiment, the modified XYR1 is a polypeptide that consists of an amino acid sequence having at least 90% identity to SEQ ID NO: 1 including at least one amino acid residue selected from the group consisting of the followings:

Tyr at a position corresponding to position 817 of SEQ ID NO: 1;

Tyr at a position corresponding to position 825 of SEQ ID NO: 1; and

Val, Ile, Leu, Phe, Trp, or Tyr, preferably Val or Trp, at a position corresponding to position 826 of SEQ ID NO: 1, and the polypeptide functions as a transcriptional activator of cellulase and hemicellulase.

The mutant filamentous fungus of the present invention can express a cellulase-based biomass-degrading enzyme, such as cellulase and hemicellulase, even in the absence of a cellulase inducer, such as cellulose, sophorose, and cellooligosaccharide. Furthermore, the mutant filamentous fungus can efficiently produce a protein even in an environment where a cellulase noninducible carbon source, such as glucose, is a main carbon source, for example, even in the absence of a cellulase inducer.

Accordingly, in one further aspect, the present invention provides a method for producing a protein using the mutant filamentous fungus of the present invention described above. In the method for producing a protein according to the present invention, the mutant filamentous fungus of the present invention is cultured. By the culture, a target protein is produced and accumulated in the culture. The target protein can be produced by separating the target protein from the culture.

Examples of the target protein to be produced include, but not limited to, a cellulase-based biomass-degrading enzyme, such as cellulase and hemicellulase; and exoglucanase, endoglucanase, β-glucosidase, protease, lipase, mannase, arabinase, galactase, and amylase. The target protein may be one protein or a mixture of a plurality of proteins. The target protein is preferably a cellulase-based biomass-degrading enzyme, more preferably cellulase and/or hemicellulase, and further preferably cellulase and hemicellulase. Examples of the hemicellulase include xylanase, β-xylosidase, and α-arabinofuranosidase. Among them, xylanase is preferable.

Alternatively, the target protein may be a heterologous protein that is not intrinsically produced by filamentous fungi. In such a case, a recombinant filamentous fungus is produced by inserting a gene coding for the heterologous protein into the mutant filamentous fungus of the present invention, and proteins including the heterologous protein can be obtained by culturing the recombinant filamentous fungus. Furthermore, secretory production of the heterologous protein in the culture is possible by operably linking a gene coding for the heterologous protein to a secretory signal peptide that functions in the filamentous fungus.

The culture medium to be used for producing the protein may be either a synthetic medium or a natural medium as long as ingredients necessary for ordinary filamentous fungal proliferation and protein production, such as a carbon source, a nitrogen source, an inorganic salt, and a vitamin, are contained.

The carbon source may be any carbon source that can be utilized by the mutant filamentous fungus, and examples thereof include carbohydrates, such as glucose and fructose; sugar alcohols, such as sorbitol; alcohols, such as ethanol and glycerol; and organic acids, such as acetic acid. These carbon sources may be used alone or in combination of two or more thereof.

Preferably, in the method for producing a protein according to the present invention, the mutant filamentous fungus is cultured in an environment where a cellulase noninducible carbon source is a main carbon source. Examples of the cellulase noninducible carbon source include glucose, fructose, sucrose, maltose, and glycerol. Among them, glucose is preferable in terms of cost. When the target protein to be produced is a cellulase-based biomass-degrading enzyme, although the culture by this method may be performed in the presence of a cellulase inducer, such as cellulose, sophorose, and cellooligosaccharide, an enhanced production of the target protein is possible even in the absence of the inducer, and the culture is not limited to the use or non-use of an inducer. In addition, since the present invention efficiently produces a protein such as a cellulase-based biomass-degrading enzyme while further reducing the catabolite repression, the mutant filamentous fungus may be cultured while feeding a noninducible carbon source such as glucose. On this occasion, it is preferable to dissolve the cellulase noninducible carbon source, for example, glucose, in an aqueous solution containing ammonia water or an ammonium salt serving as a nitrogen source and to perform culture while feeding the solution, in terms of culture efficiency and suppression of foaming during culturing.

Examples of the nitrogen source include ammonia, an ammonium salt such as ammonium sulfate, a nitrogen compound such as amine, and a natural nitrogen source such as peptone and soybean hydrolysate.

Examples of the inorganic salt include potassium phosphate, magnesium sulfate, sodium chloride, ferrous sulfate, and potassium carbonate.

Examples of the vitamin include biotin and thiamine. Furthermore, a substance required for growth of the filamentous fungus of the present invention can be added as needed.

The culture is preferably performed in aerobic conditions such as shaking culture and aeration agitation culture. The culture temperature is preferably 10° C. or more, more preferably 20° C. or more, and more preferably 25° C. or more and preferably 50° C. or less, more preferably 42° C. or less, and more preferably 35° C. or less, and is preferably from 10° C. to 50° C., more preferably from 20° C. to 42° C., and more preferably from 25° C. to 35° C. The pH during culturing is from 3 to 9 and preferably from 4 to 5. The culture time is from 10 hours to 10 days and preferably from 2 to 7 days.

After the culture, the target protein is separated from the resulting culture by a common method. For example, the target protein can be separated from the culture by collecting the culture, performing cell disruption treatment, such as ultrasonication or pressurization as needed, and performing an appropriate combination of filtration, centrifugation, ultrafiltration, salting out, dialysis, chromatography, etc. The degree of separation of the target protein is not particularly limited. For example, the culture supernatant or its roughly separated and purified product can be obtained as a composition containing the target protein.

The present invention also encompasses the following materials, producing methods, uses, methods, and so on as exemplary embodiments. However, the present invention is not limited to these embodiments.

[1] A method for producing a mutant filamentous fungus, comprising:
  modifying XYR1 and ACE3 expression in a parent filamentous fungus, wherein
  the modification of XYR1 is substitution, deletion, insertion, or addition of at least one amino acid residue in a region corresponding to positions 810 to 833 of SEQ ID NO: 1 in a polypeptide that consists of SEQ ID NO: 1 or an amino acid sequence having at least 90% identity thereto and functions as a transcriptional activator of cellulase and hemicellulase, and
  the modification of ACE3 expression is enhanced expression of a polypeptide that consists of the amino acid sequence at positions 107 to 734 of SEQ ID NO: 3 or an amino acid sequence having at least 90% identity thereto and functions as a transcriptional activator of cellulase and hemicellulase.

[2] The method according to [1], wherein
  the at least one amino acid residue is:
  preferably at least one selected from the group consisting of Val, Ile, Leu, Ala, Gly, Thr, and Glu; more preferably at least one selected from the group consisting of the following (1) and (2): (1) Val, Ile, or Leu, and (2) Ala or Gly, or at least one selected from the group consisting of Val, Ala, Thr, and Glu;
  further preferably at least one selected from the group consisting of Val and Ala; and
  preferably the at least one amino acid residue is substituted.

[3] The method according to [2], wherein the at least one amino acid residue is preferably at least one selected from the group consisting of the amino acid residues at positions corresponding to 817, 821, 824, 825, and 826 of SEQ ID NO: 1.

[4] The method according to [2] or [3], wherein the at least one amino acid residue is substituted with Val, Glu, Ile, Leu, Lys, Phe, Thr, Trp, or Tyr.

[5] The method according to any one of [2] to [4], wherein the substitution of at least one amino acid residue is:
  preferably at least one selected from the group consisting of the followings:
  substitution of Val with Lys, Phe, Trp, or Tyr;
  substitution of Ile with Phe, Trp, or Tyr;
  substitution of Leu with Phe, Trp, or Tyr;
  substitution of Ala with Val, Glu, Ile, Leu, Lys, Phe, Thr, Trp, or Tyr;
  substitution of Gly with Val, Ile, Leu, Phe, Trp, or Tyr;
  substitution of Thr with Tyr; and
  substitution of Glu with Tyr, and
  more preferably at least one selected from the group consisting of the followings:
  substitution of Gly at a position corresponding to position 812 of SEQ ID NO: 1 with Val, Ile, Leu, Phe, Trp, or Tyr;
  substitution of Val at a position corresponding to position 814 of SEQ ID NO: 1 with Phe, Trp, or Tyr;
  substitution of Ala at a position corresponding to position 816 of SEQ ID NO: 1 with Val, Ile, Leu, Phe, Trp, or Tyr;
  substitution of Thr at a position corresponding to position 817 of SEQ ID NO: 1 with Tyr;
  substitution of Ala at a position corresponding to position 820 of SEQ ID NO: 1 with Val, Ile, Leu, Phe, Trp, or Tyr;
  substitution of Val at a position corresponding to position 821 of SEQ ID NO: 1 with Lys, Phe, Trp, or Tyr;
  substitution of Ala at a position corresponding to position 823 of SEQ ID NO: 1 with Val, Ile, Leu, Phe, Trp, or Tyr;
  substitution of Ala at a position corresponding to position 824 of SEQ ID NO: 1 with Val, Glu, Ile, Leu, Lys, Phe, Thr, Trp, or Tyr;
  substitution of Glu at a position corresponding to position 825 of SEQ ID NO: 1 with Tyr;
  substitution of Ala at a position corresponding to position 826 of SEQ ID NO: 1 with Val, Ile, Leu, Phe, Trp, or Tyr;
  substitution of Ile at a position corresponding to position 827 of SEQ ID NO: 1 with Phe, Trp, or Tyr;
  substitution of Ile at a position corresponding to position 830 of SEQ ID NO: 1 with Phe, Trp, or Tyr; and
  substitution of Leu at a position corresponding to position 831 of SEQ ID NO: 1 with Phe, Trp, or Tyr.

[6] The method according to [5], wherein
  the substitution of at least one amino acid residue is preferably at least one selected from the group consisting of the followings:
  substitution of Thr at a position corresponding to position 817 of SEQ ID NO: 1 with Tyr;

substitution of Val at a position corresponding to position 821 of SEQ ID NO: 1 with Lys, Phe, Trp, or Tyr;

substitution of Ala at a position corresponding to position 824 of SEQ ID NO: 1 with Val, Glu, Ile, Leu, Lys, Phe, Thr, Trp, or Tyr;

substitution of Glu at a position corresponding to position 825 of SEQ ID NO: 1 with Tyr; and substitution of Ala at a position corresponding to position 826 of SEQ ID NO: 1 with Val, Ile, Leu, Phe, Trp, or Tyr.

[7] The method according to any one of [1] to [6], wherein the amino acid sequence at positions 107 to 734 of SEQ ID NO: 3 or an amino acid sequence having at least 90% identity thereto:

preferably preserves all amino acid residues of a region corresponding to positions 725 to 728 of SEQ ID NO: 3, and more preferably preserves all amino acid residues of a region corresponding to positions 718 to 728 of SEQ ID NO: 3; or preferably preserves a region corresponding to positions 724 to 734 of SEQ ID NO: 3, provided that a part of amino acid residues in the region may be mutated.

[8] The method according to any one of [1] to [7], wherein the enhanced expression of the polypeptide is preferably performed by improving the transcription level of the gene coding for the polypeptide.

[9] The method according to [8], wherein the improvement in the transcription level of the gene coding for the polypeptide is performed by introducing the gene coding for the polypeptide operably linked to a control region into a parent filamentous fungus.

[10] The method according to any one of [1] to [9], wherein when the XYR1 is a polypeptide consisting of the amino acid sequence of SEQ ID NO: 51 registered as NCBI Reference Sequence: XP_006966092.1, or a polypeptide consisting of an amino acid sequence having at least 90% identity to the amino acid sequence of SEQ ID NO: 51 and functioning as a transcriptional activator of cellulase and hemicellulase, the substitution of at least one amino acid residue is preferably at least one selected from the group consisting of the followings:

substitution of Thr at a position corresponding to position 797 of SEQ ID NO: 51 with Tyr;

substitution of Val at a position corresponding to position 801 of SEQ ID NO: 51 with Lys, Phe, Trp, or Tyr;

substitution of Ala at a position corresponding to position 804 of SEQ ID NO: 51 with Val, Glu, Ile, Leu, Lys, Phe, Thr, Trp, or Tyr;

substitution of Glu at a position corresponding to position 805 of SEQ ID NO: 51 with Tyr; and substitution of Ala at a position corresponding to position 806 of SEQ ID NO: 51 with Val, Ile, Leu, Phe, Trp, or Tyr.

[11] The method according to any one of [1] to [10], wherein the mutant filamentous fungus:

preferably alleviates catabolite repression compared to the parent filamentous fungus, and more preferably expresses cellulase in the absence of a cellulase inducer.

[12] The method according to any one of [1] to [11], wherein the filamentous fungus is preferably a *Trichoderma* fungus.

[13] The method according to [12], wherein the *Trichoderma* fungus is preferably *Trichoderma reesei* or its mutant strain.

[14] A method for producing a protein, comprising culturing the filamentous fungus produced by the method according to any one of [1] to [13].

[15] The method according to [14], wherein the protein is preferably cellulase and/or hemicellulase.

[16] The method according to [14] or [15], wherein the culture is preferably performed in the presence of glucose.

[17] A mutant filamentous fungus comprising modified XYR1 and showing enhanced expression of a partial polypeptide of ACE3 compared to a parent filamentous fungus, wherein the modified XYR1 is a polypeptide having a substitution, deletion, insertion or addition of at least one amino acid residue in a region corresponding to positions 810 to 833 of SEQ ID NO: 1 in the amino acid sequence of SEQ ID NO: 1 or an amino acid sequence having at least 90% identity thereto, and the polypeptide functions as a transcriptional activator of cellulase and hemicellulase, and the partial polypeptide of ACE3 is a polypeptide that consists of the amino acid sequence at positions 107 to 734 of SEQ ID NO: 3 or an amino acid sequence having at least 90% identity thereto and functions as a transcriptional activator of cellulase and hemicellulase.

[18] The mutant filamentous fungus according to [17], wherein the amino acid sequence at positions 107 to 734 of SEQ ID NO: 3 or an amino acid sequence having at least 90% identity thereto:

preferably preserves all amino acid residues of a region corresponding to positions 725 to 728 of SEQ ID NO: 3, and more preferably preserves all amino acid residues of a region corresponding to positions 718 to 728 of SEQ ID NO: 3; or preferably preserves a region corresponding to positions 724 to 734 of SEQ ID NO: 3, provided that a part of amino acid residues in the region may be mutated.

[19] The mutant filamentous fungus according to [17] or [18], wherein the modified XYR1 is preferably a polypeptide having a substitution, deletion, insertion or addition of at least one amino acid residue in a region corresponding to positions 810 to 833 of SEQ ID NO: 1 in the amino acid sequence of SEQ ID NO: 1 or an amino acid sequence having at least 90% identity thereto, the substitution being selected from the group consisting of the followings:

substitution of Val with Lys, Phe, Trp, or Tyr;

substitution of Ile with Phe, Trp, or Tyr;

substitution of Leu with Phe, Trp, or Tyr;

substitution of Ala with Val, Glu, Ile, Leu, Lys, Phe, Thr, Trp, or Tyr;

substitution of Gly with Val, Ile, Leu, Phe, Trp, or Tyr;

substitution of Thr with Tyr; and substitution of Glu with Tyr, and and the polypeptide functions as a transcriptional activator of cellulase and hemicellulase.

The mutant filamentous fungus according to [19], wherein the modified XYR1 is preferably a polypeptide that consists of an amino acid sequence having at least 90% identity to SEQ ID NO: 1 including at least one amino acid residue selected from the group consisting of the following (a) to (m):

(a) Val, Ile, Leu, Phe, Trp, or Tyr at a position corresponding to position 812 of SEQ ID NO: 1;

(b) Phe, Trp, or Tyr at a position corresponding to position 814 of SEQ ID NO: 1;

(c) Val, Ile, Leu, Phe, Trp, or Tyr at a position corresponding to position 816 of SEQ ID NO: 1;

(d) Tyr at a position corresponding to position 817 of SEQ ID NO: 1;

(e) Val, Ile, Leu, Phe, Trp, or Tyr at a position corresponding to position 820 of SEQ ID NO: 1;

(f) Lys, Phe, Trp, or Tyr at a position corresponding to position 821 of SEQ ID NO: 1;

(g) Val, Ile, Leu, Phe, Trp, or Tyr at a position corresponding to position 823 of SEQ ID NO: 1;

(h) Val, Glu, Ile, Leu, Lys, Phe, Thr, Trp, or Tyr at a position corresponding to position 824 of SEQ ID NO: 1;

(i) substitution of Glu Tyr at a position corresponding to position 825 of SEQ ID NO: 1 with Tyr;

(j) Val, Ile, Leu, Phe, Trp, or Tyr at a position corresponding to position 826 of SEQ ID NO: 1;

(k) Phe, Trp, or Tyr at a position corresponding to position 827 of SEQ ID NO: 1;

(l) Phe, Trp, or Tyr at a position corresponding to position 830 of SEQ ID NO: 1; and (m) Phe, Trp, or Tyr at a position corresponding to position 831 of SEQ ID NO: 1, and the polypeptide functions as a transcriptional activator of cellulase and hemicellulase.

[21] The mutant filamentous fungus according to [20], wherein the modified XYR1 is preferably a polypeptide that consists of an amino acid sequence having at least 901 identity to SEQ ID NO: 1 including at least one amino acid residue selected from the group consisting of the followings:

Lys, Phe, Trp, or Tyr, preferably Phe, and more preferably Lys or Tyr at a position corresponding to position 821 of SEQ ID NO: 1; and Val, Glu, Ile, Leu, Lys, Phe, Thr, Trp, or Tyr, preferably Val, and more preferably Glu, Ile, Leu, Lys, Phe, Thr, Trp, or Tyr at a position corresponding to position 824 of SEQ ID NO: 1, and the polypeptide functions as a transcriptional activator of cellulase and hemicellulase.

[22] The mutant filamentous fungus according to [20] or [21], wherein the modified XYR1 is preferably a polypeptide that consists of an amino acid sequence having at least 90% identity to SEQ ID NO: 1 including at least one amino acid residue selected from the group consisting of the followings:

Tyr at a position corresponding to position 817 of SEQ ID NO: 1;

Tyr at a position corresponding to position 825 of SEQ ID NO: 1; and

Val, Ile, Leu, Phe, Trp, or Tyr, preferably Val or Trp, at a position corresponding to position 826 of SEQ ID NO: 1, and the polypeptide functions as a transcriptional activator of cellulase and hemicellulase.

EXAMPLES

The present invention will now be further specifically described using examples.

Example 1 Construction of Plasmid DNA for Gene Introduction

The following DNA fragments 1 to 5 were prepared by PCR using a genomic DNA of *Trichoderma reesei* as a template. Fragment 1: a promotor region of about 1.5 kbp upstream of act1 gene (TRIREDRAFT_44504); Fragment 2: xyr1 gene (SEQ ID NO: 2, about 3.0 kbp); Fragment 3: a polynucleotide (a nucleotide region from the 881st to 2918th of SEQ ID NO: 4, about 2.0 kbp) coding for a partial polypeptide of ACE3 (positions 107 to 734 of SEQ ID NO: 3); Fragment 4: a terminator region of about 0.6 kbp downstream of cbh1 gene (TRIREDRAFT_44504); and Fragment 5: a region of about 2.7 kbp of pyr4 gene (TRIREDRAFT_74020).

The fragments 1 and 2 were linked to construct a cassette 1: Pact1-XYR1. The fragments 1 and 3 were linked to construct a cassette 2: Pact1-ACE3. A fragment 6 of about 0.5 kbp and a fragment 7 of about 1.0 kbp were located upstream and downstream, respectively, of the fragment 5 as homologous sequences for pop-out to prepare a transformation marker fragment. The fragment 4 and the transformation marker fragment were linked to construct a cassette 3: Tcbh1-pyr4. The linking of DNA fragments was performed according to the protocol of In-Fusion HD Cloning Kit (Takara Bio Inc.). The constructed cassettes, the DNA fragments contained therein, and the primers used for constructing the cassettes are shown in Table 1.

The cassettes 1 and 3 were linked and inserted into the HincII restriction enzyme breakpoint of pUC118 (Takara Bio Inc.) to construct an xyr1 steady expression plasmid pUC-Pact1-XYR1. The cassettes 2 and 3 were linked and inserted into the HincII restriction enzyme breakpoint of pUC118 (Takara Bio Inc.) to construct an ace3 steady expression plasmid pUC-Pact1-ACE3.

TABLE 1

| | Cassette | | | Primers (5'-3' sequences) | SEQ ID NO: |
|---|---|---|---|---|---|
| Cassette 1 Pact1-xyr1 | Fragment 1 | ca. 1.5 kbp | | Fw ACGGGGTACGCGTGAAATTG | 5 |
| | | | | Rv TGTGACTGATTAATGTATGA | 6 |
| | Fragment 2 | ca. 3.0 kbp | | Fw CATTAATCAGTCACAATGTTGTCCAATCCTC TCCG | 7 |
| | | | | Rv TTTCGCCACGGAGCTTTAGAGGGCCAGACCG GTTC | 8 |
| Cassette 2 Pact-ace3 | Fragment 1 | ca. 1.5 kbp | | Fw ACGGGGTACGCGTGAAATTG | 5 |
| | | | | Rv TGTGACTGATTAATGTATGA | 6 |
| | Fragment 3 | ca. 2.0 kbp | | Fw CATTAATCAGTCACAATGCTGCGCTACTCCC CCGT | 9 |
| | | | | Rv TTTCGCCACGGAGCTTTAGCCAACAACGGTA GTGG | 10 |

TABLE 1-continued

| | Cassette | | | Primers (5'-3' sequences) | SEQ ID NO: |
|---|---|---|---|---|---|
| Cassette 3 | Fragment | ca. | 0.6 | Fw AGCTCCGTGGCGAAAGCCTG | 11 |
| Tcbh1- | 4 | kbp | | Rv CTCGGCTACGTTGTCATCGT | 12 |
| pyr4 | Fragment | ca. | 2.7 | Fw CAAACCAGCCAAGGTAGGTA | 13 |
| | 5 | kbp | | Rv TTGGTTCTTGGTTTGGAGGG | 14 |
| | Fragment | ca. | 0.5 | Fw GACAACGTAGCCGAGAAGTACCGCGCGCTTG | 15 |
| | 6 | kbp | | Rv ACCTTGGCTGGTTTGCTGAATGCCCGGTGGT AAGC | 16 |
| | Fragment | ca. | 1.0 | Fw AAGTACCGCGCGCTTGACAA | 17 |
| | 7 | kbp | | Rv TTGGTTCTTGGTTTGGAGGG | 18 | pUC-Pact1-XYR1(V821F) and pUC-Pact1-XYR1 (A824V) were respectively constructed by PCR using the pUC-Pact1-XYR1 as a template and the primers shown in Table 2. The pUC-Pact1-XYR1(V821F) is a plasmid coding for mutant XYR1(V821F) having amino acid substitution, V821F, in the amino acid sequence of SEQ ID NO: 2. The pUC-Pact1-XYR1(A824V) is a plasmid coding for mutant XYR1(A824V) having amino acid substitution, A824V, in the amino acid sequence of SEQ ID NO: 2.

TABLE 2

| Substitution | | Primers (5'-3' sequences) | SEQ ID NO: |
|---|---|---|---|
| V821F | Fw | CACGCGTTCTCGGCTGCCGAAGCTATT | 19 |
| | Rv | AGCCGAGAACGCGTGGCTCGTCGCCGT | 20 |
| A824V | Fw | TCGGCTGTCGAAGCTATTAGCCAGATT | 21 |
| | Rv | AGCTTCGACAGCCGATACCGCGTGGCT | 22 |

The constructed plasmids pUC-Pact1-ACE3, pUC-Pact1-XYR1(V821F), and pUC-Pact1-XYR1(A824V) were replicated. The plasmids were introduced into competent cells *Escherichia coli* DH5a Competent Cells (Takara Bio Inc.), the cells were cultured in an LB medium containing ampicillin (37° C., 1 day), and the plasmids were collected and purified from the cultured cells using NucleoSpin™ Plasmid (Macherey-Nagel GmbH & Co. KG).

Example 2 Production of Filamentous Fungus Mutant Strain

*Trichoderma reesei* JN13Δpyr4 strain was transformed by introduction of the plasmids constructed in Example 1. The plasmid introduction was performed by a protoplast PEG method (Biotechnol. Bioeng., 2012, 109 (1):92-99). The transformant was selected using the pyr4 gene as a marker with a selection medium (2% glucose, 1.1 M sorbitol, 2% agar, 0.2% $KH_2PO_4$ (pH 5.5), 0.06% $CaCl_2.2H_2O$, 0.06% $CsCl_2$, 0.06, $MgSO_4.7H_2O$, 0.5% $(NH_4)_2SO_4$, 0.1% Trace element 1; % is w/v % in every ingredient). The composition of the trace element 1 was as follows: 0.5 g of $FeSO_4.7H_2O$, 0.2 g of $CoCl_2$, 0.16 g of $MnSO_4$. $H_2O$, and 0.14 g of $ZnSO_4.7H_2O$ were diluted up to 100 mL with distilled water. Those in which the target gene fragments were inserted were verified by PCR of the resulting transformants to obtain a JN13_ACE3 strain in which the pUC-Pact1-ACE3 was introduced and a JN13_XYR1(V821F) strain in which pUC-Pact1-XYR1(V821F) was introduced. The JN13_ACE3 strain highly expresses ACE3 by the ace3 steady expression plasmid pUC-Pact1-ACE3. The JN13_XYR1(V821F) strain expresses mutant XYR1(V821F).

In order to transform the transformant again, a strain that acquired resistance to 5-fluoroorotic acid (5-FOA) and grew was selected again using a PDA medium containing 0.2% 5-FOA monohydrate. That is, spores of the JN13_ACE3 strain were applied to a 5-FOA-containing medium, and the grown strain was acquired as a JN13_ACE3Δpyr4 strain. The acquired strain was transformed with the pUC-Pact1-XYR1(V821F) or pUC-Pact1-XYR1(A824V) to obtain a JN13_XYR1(V821F)+ACE3 strain and a JN13_XYR1(A824V)+ACE3 strain. These strains highly express ACE3 and express mutant XYR1(V821F or A824V).

Example 3 Culture of Filamentous Fungus Mutant Strain

The filamentous fungus strains obtained in Example 2 were each cultured to produce proteins. In the pre-culture, 50 mL of a medium was placed in a 500-mL flask, the spores of the strains produced in Example 2 were inoculated at $1 \times 10^5$ spores/mL, and shaking culture was performed at 28° C. and at 220 rpm (PRXYg-98R, manufactured by Preci Co., Ltd.). The medium composition was as follows: 1% glucose, 0.14% $(NH_4)_2SO_4$, 0.2% $KH_2PO_4$, 0.03% $CaCl_2.2H_2O$, 0.03% $MgSO_4.7H_2O$, 0.1% Hipolypepton N, 0.05% Bacto Yeast extract, 0.1% Tween 80, 0.1% Trace element 2, and 50 mM tartaric acid buffer (pH 4.0) (% is w/v % in every ingredient). The composition of the trace element 2 was as follows: 6 mg $H_3BO_3$, 26 mg $(NH_4)_6Mo_7O_{24}.4H_2O$, 100 mg $FeCl_3.6H_2O$, 40 mg $CuSO_4.5H_2O$, 8 mg $MnCl_2.4H_2O$, and 200 mg $ZnCl_2$ were diluted up to 100 mL with distilled water.

After the pre-culture for 2 days, main culture was performed. 50 mL of a medium was placed in a 500-mL flask, the pre-culture solution was inoculated at 1% (v/v %), and culture was performed at 28° C. at 220 rpm for 4 days. The medium composition was as follows: 3% cellulose or 31 glucose, 0.14% $(NH_4)_2SO_4$, 0.2% $KH_2PO_4$, 0.03% $CaCl_2.2H_2O$, 0.03% $MgSO_4.7H_2O$, 0.1% Hipolypepton N, 0.05% Bacto Yeast extract, 0.1, Tween 80, 0.1% Trace element 2, 1.28% diammonium hydrogen citrate, and 50 mM tartaric acid buffer (pH 4.0) (% is w/v %) in every ingredient).

Example 4 Protein Concentration Measurement

The concentrations of the proteins of the cultures in Example 3 were measured by a bradford method. In the bradford method, Quick Start Protein Assay (Bio-Rad Laboratories, Inc.) was used, and each protein amount was calculated based on a calibration curve formed using bovine γ-globulin as a standard protein. FIG. 1 shows the relative protein productivity of each strain when the protein productivity of the JN13 strain (parent strain) in the culture using glucose only as the carbon source (glucose culture) was defined as 1. The protein productivity of the parent strain alone mutant strain and ACE3 high level expression strain, and the productivities of CBH1, CBH2, and EG1, which are main cellulase enzymes, were drastically improved.

TABLE 3

|  | JN13 Cellulose | JN13 | XYR1 (V821F) | ACE3 | XYR1 (V821F) + ACE3 | XYR1 (A824V) + ACE3 |
|  |  |  |  | Glucose |  |  |
| --- | --- | --- | --- | --- | --- | --- |
| BXL1 | 2.1 | 0.2 | 10.5 | 0.7 | 9.2 | 5.0 |
| CBH1 | 27.6 | 5.6 | 5.4 | 21.3 | 18.6 | 22.4 |
| CBH2 + EG1 | 25.5 | 6.9 | 6.8 | 15.7 | 15.9 | 17.9 |
| XYN1 + XYN2 | 6.2 | 4.7 | 48.1 | 6.0 | 26.8 | 20.1 |
| others | 38.5 | 82.7 | 29.2 | 56.4 | 29.4 | 34.7 |

JN13 in the glucose culture was significantly decreased compared to the culture in the presence of cellulose. It is inferred that this is because since there is no inducer when only glucose is used as the carbon source, the expression of the cellulase group and xylanase group is not induced for transcription activation. In the XYR1(V821F)+ACE3 strain and XYR1(A824V)+ACE3 strain in which both XYR1 and ACE3 were modified, the protein productivity in the glucose culture was significantly improved compared to the parent strain and also further compared to the XYR1(V821F) strain and ACE3 strain in which only one of XYR1 and ACE3 was modified.

Example 5 Protein Composition Analysis

Figure 2:
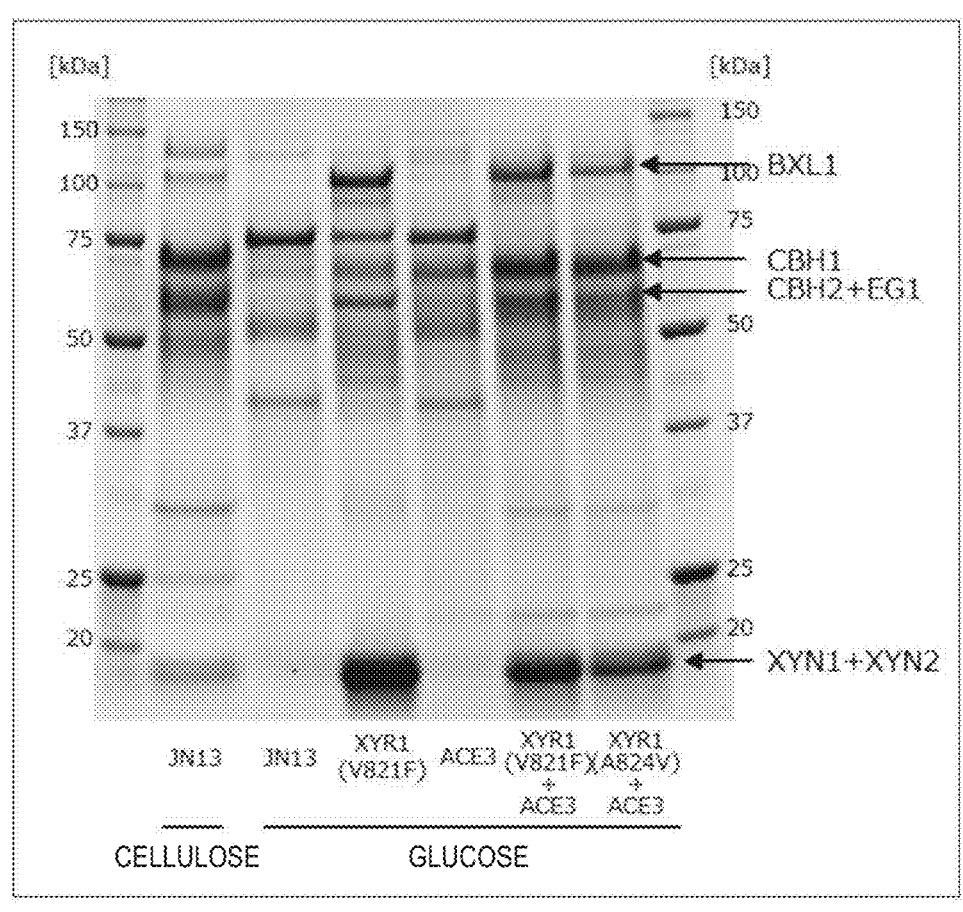
FIG. 2 shows the protein composition analysis, gel elec-
trophoresis images, of the culture of mutant filamentous
fungus strains.

The protein composition of each of the cultures in Example 3 was analyzed. The analysis used Mini PRO-TEAN TGX Stain-Free Gels (Any KD, 15 wells, Bio-Rad Laboratories, Inc.). As the standard, Precision Plus Protein Unstained standard was used. The culture of Example 3 appropriately diluted was mixed with a buffer, treated at 99° C. for 5 minutes, and applied to a gel, followed by electrophoresis at 200 V for 35 minutes. The band intensity ratios were calculated from the resulting image file (FIG. 2) using analysis software (Image Lab), and the composition ratios of the produced proteins were calculated. The amount of each protein produced was determined from the composition ratio and the protein concentration determined in Example 4. Subsequently, the relative productivity of each protein in each strain was calculated using the protein productivity of XYR1 mutation only (XYR1(V821F) strain) as 1.

Figure 3:
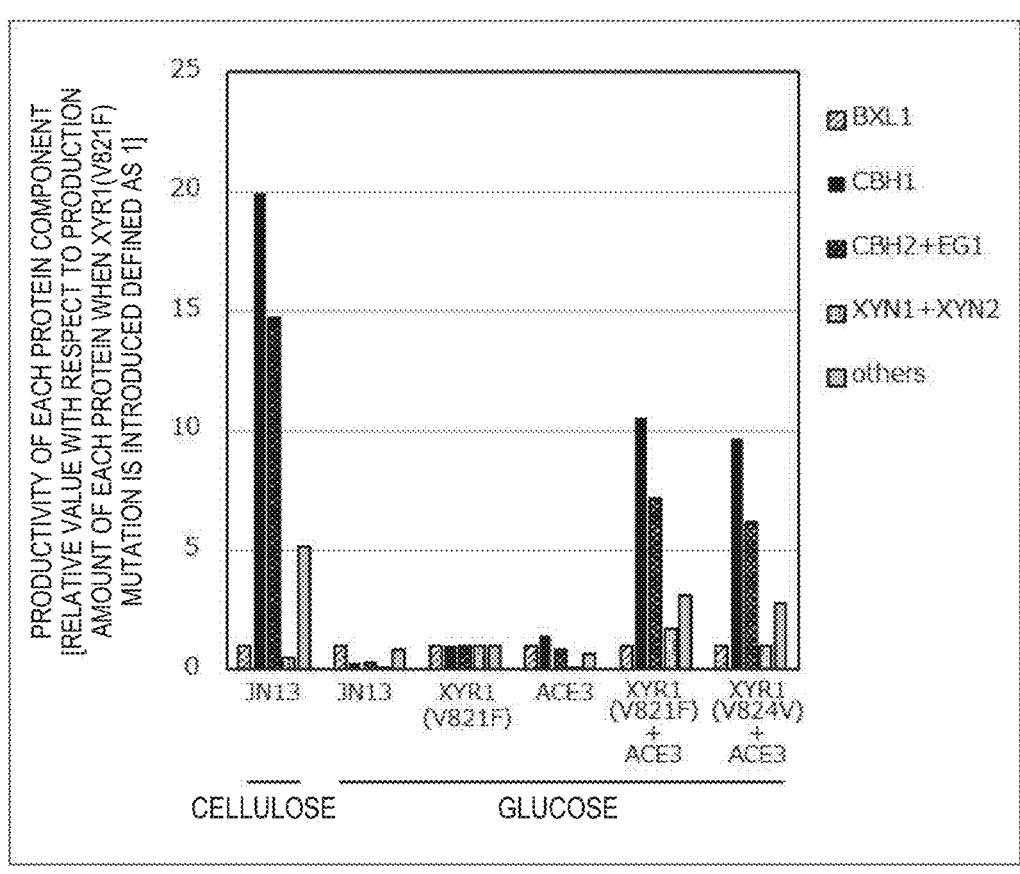
FIG. 3 shows relative productivity of each protein in
mutant filamentous fungus strains.

Regarding the proteins produced in each strain, the composition ratios are shown in Table 3, and the relative productivities are shown in FIG. 3. In the glucose culture, the JN13 strain (parent strain) almost did not produce cellulase and xylanase (BXL1, CBH1, CBH2+EG1, XYN1+XYN2). In the XYR1 alone mutant strain (XYR1(V821F)), xylanase (XYN1+XYN2) such as XYN1+XYN2 was mainly produced. In the ACE3 high level expression strain (ACE3), although the ratios of cellulase, such as CBH1, CBH2, and EG1, were improved, as shown in FIG. 1, the total amount of proteins produced was low compared to the XYR1 alone mutant strain and was the same level as the parent strain. In the strains (XYR1(V821F)+ACE3 and XYR1(A824V)+ACE3) in which XYR1 mutation and ACE3 high level expression were combined, cellulase and xylanase were produced even in the glucose culture. In XYR1(V821F)+ACE3 and XYR1(A824V)+ACE3, the composition ratios of the products were closer to the parent strain in the presence of cellulose compared to the XYR1

Example 6 Production of Filamentous Fungus Mutant Strain

A plasmid pUC-Pact1-XYR1(T817Y) that expresses mutant XYR1 having amino acid substitution of T817Y was constructed by the same procedure as in Example 1 by PCR using pUC-Pact1-XYR1 as a template and primers of SEQ ID NOs: 23 and 24 shown in Table 4. Plasmids expressing mutant XYR1 having amino acid substitution of V821Y, V821K, A824I, A824L, A824F, A824W, A824Y, A824T, A824K, A824E, E825Y, A826V, or A826W were constructed by the same procedure using the primers shown in Table 4. The JN13_ACE3Δpyr4 strain was transformed with the constructed plasmids by the same method as in Example 2 to obtain filamentous fungus mutant strains in which ACE3 and the mutant XYR1 were introduced.

TABLE 4

| Substitution | Primers (5'-3' sequences) |  | SEQ ID NO: |
| --- | --- | --- | --- |
| T817Y | Fw | ACGGCCTACAGCCACGCGGTATCGGCT | 23 |
|  | Rv | GTGGCTGTACGCCGTCACGAATCCTTC | 24 |
| V821Y | Fw | CACGCGTACTCGGCTGCCGAAGCTATT | 25 |
|  | Rv | AGCCGAGTACGCGTGGCTCGTCGCCGT | 26 |
| V821K | Fw | CACGCGAAGTCGGCTGCCGAAGCTATT | 27 |
|  | Rv | AGCCGACTTCGCGTGGCTCGTCGCCGT | 28 |
| A824I | Fw | TCGGCTATCGAAGCTATTAGCCAGATT | 29 |
|  | Rv | AGCTTCGATAGCCGATACCGCGTGGCT | 30 |
| A824L | Fw | TCGGCTCTCGAAGCTATTAGCCAGATT | 31 |
|  | Rv | AGCTTCGAGAGCCGATACCGCGTGGCT | 32 |
| A824F | Fw | TCGGCTTTCGAAGCTATTAGCCAGATT | 33 |
|  | Rv | AGCTTCGAAAUUCGATACCGCGTGGCT | 34 |
| A824W | Fw | TCGGCTTGGGAAGCTATTAGCCAGATT | 35 |
|  | Rv | AGCTTCCCAAGCCCATACCGCGTGGCT | 36 |
| A824Y | Fw | TCGGCTTACGAAGCTATTAGCCAGATT | 37 |
|  | Rv | AGCTTCGTAAGCCGATACCGCGTGGCT | 38 |
| A824T | Fw | TCGGCTACCGAAGCTATTAGCCAGATT | 39 |
|  | Rv | AGCTTCGGTAGCCGATACCGCGTGGCT | 40 |
| A824K | Fw | TCGGCTAAGGAAGCTATTAGCCAGATT | 41 |
|  | Rv | AGCTTCCTTAGCCGATACCGCGTGGCT | 42 |
| A824E | Fw | TCGGCTGAGGAAGCTATTAGCCAGATT | 43 |
|  | Rv | AGCTTCCTCAGCCGATACCGCGTGGCT | 44 |
| E825Y | Fw | GCTGCCTACGCTATTAGCCAGATTCTC | 45 |
|  | Rv | AATAGCGTAGGCAGCCGATACCGCGTG | 46 |

TABLE 4-continued

| Substitution | | Primers (5'-3' sequences) | SEQ ID NO: |
|---|---|---|---|
| A826V | Fw | GCCGAAGTCATTAGCCAGATTCTCGAG | 47 |
| | Rv | GCTAATGACTTCGGCAGCCGATACCGC | 48 |
| A826W | Fw | GCCGAATGGATTAGCCAGATTCTCGAG | 49 |
| | Rv | GCTAATCCATTCGGCAGCCGATACCGC | 50 |

The mutant strains obtained above and the JN13_XYR1 (V821F)+ACE3 strain, JN13_XYR1(A824V)+ACE3 strain, XYR1 alone mutant strain (JN13_XYR1(V821F)), and ACE3 high level expression strain (JN13_ACE3) produced in Example 2 were glucose cultured according to the method of Example 3. Subsequently, the protein concentration measurement and protein composition analysis of the culture were performed according to the methods described in Examples 4 and 5.

Figure 4:
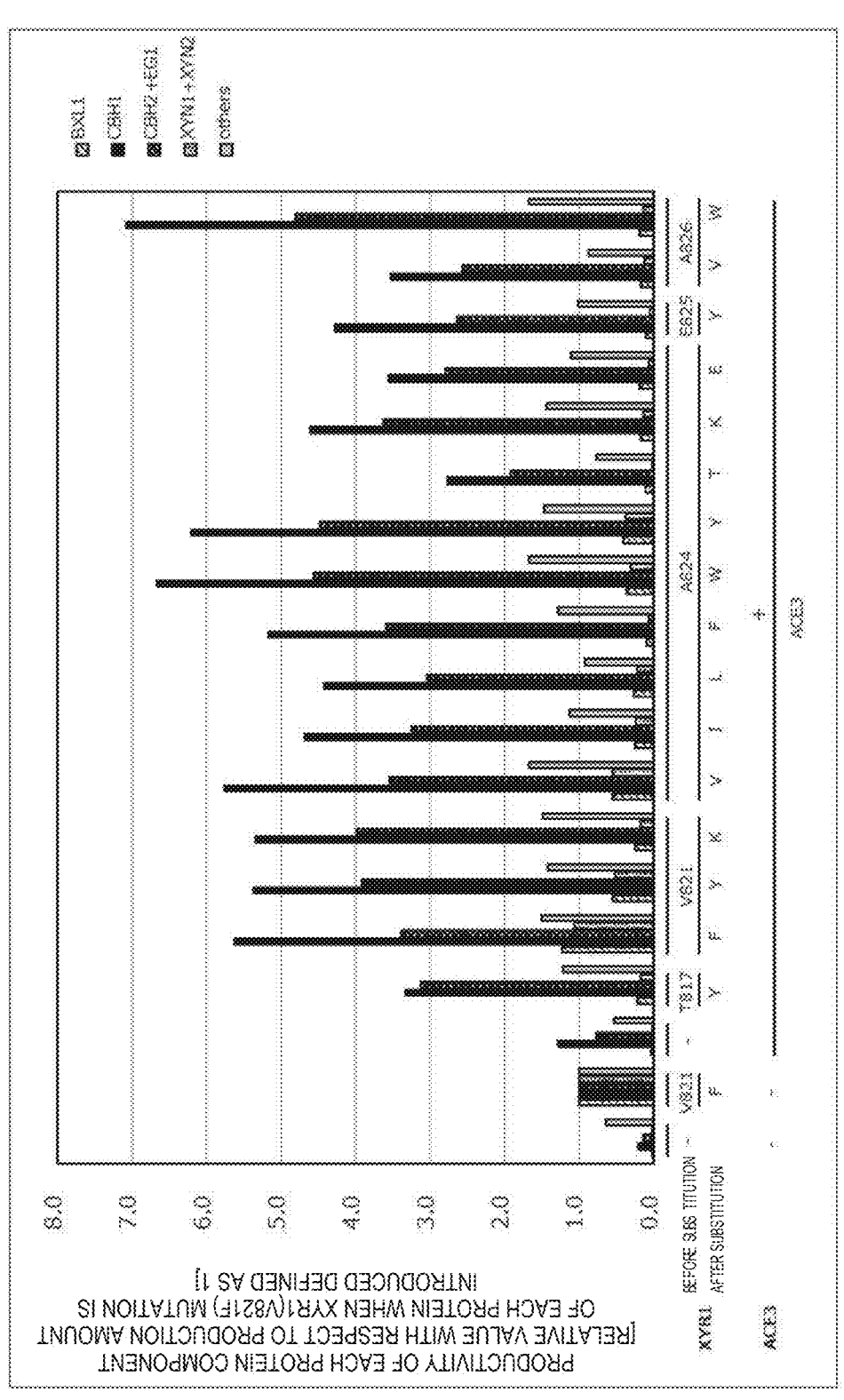
FIG. 4 shows relative productivity of each protein in
mutant filamentous fungus strains.

Regarding the proteins produced in each strain, the composition ratios are shown in Table 5, and the relative productivities are shown in FIG. 4. In FIG. 4, BXL1 is β-xylosidase BXL1, CBH1 is cellulase CBH1, CBH2+EG1 is cellulase CBH2 and EG1, XYN1+XYN2 is xylanase XYN1 and XYN2, and others are other proteins. The filamentous fungus mutant strains highly expressing ACE3 and expressing mutant XYR1 (T817Y, V821Y, V821K, A824I, A824L, A824F, A824W, A824Y, A824T, A824K, A824E, E825Y, A826V, or A826W) produced in this Example all produced proteins with the same compositions as in the JN13_XYR1(V821F)+ACE3 strain and JN13_XYR1 (A824V)+ACE3 strain produced in Example 2. In addition, in all these filamentous fungus mutant strains, the productivities of CBH1, CBH2, and EG1, which are main cellulase enzymes, were drastically improved in the glucose culture, compared to XYR1 alone mutant strain (JN13_XYR1 (V821F)) and ACE3 high level expression strain (JN13 ACE3).

TABLE 5

| | | Glucose | | | | | | | |
|---|---|---|---|---|---|---|---|---|---|
| | — | — | ACE3 — | ACE3 V821F | ACE3 A824V | ACE3 V821Y | ACE3 A824W | ACE3 A824I | ACE3 A824L | ACE3 A824Y |
| | — | V821F | | | | | | | | |
| BXL1 | 0.3 | 12.0 | 1.1 | 9.3 | 5.0 | 5.2 | 3.3 | 3.2 | 3.9 | 3.9 |
| CBH1 | 5.1 | 5.1 | 23.8 | 18.1 | 22.4 | 22.2 | 26.3 | 26.5 | 27.6 | 25.4 |
| CBH2 + EG1 | 4.7 | 6.7 | 18.6 | 14.2 | 17.9 | 21.0 | 23.4 | 23.9 | 24.7 | 24.0 |
| XYN1 + XYN2 | 2.8 | 48.8 | 3.7 | 32.5 | 20.1 | 20.1 | 11.6 | 12.2 | 12.7 | 14.4 |
| others | 87.0 | 27.5 | 52.8 | 25.9 | 34.7 | 31.4 | 35.5 | 34.1 | 31.1 | 32.4 |

| | Glucose | | | | | | | | |
|---|---|---|---|---|---|---|---|---|---|
| | ACE3 A826V | ACE3 A826W | ACE3 A824F | ACE3 V821K | ACE3 A824T | ACE3 A824K | ACE3 A824E | ACE3 T817Y | ACE3 E825Y |
| BXL1 | 3.0 | 1.7 | 1.2 | 2.7 | 2.4 | 2.2 | 3.0 | 3.1 | 1.9 |
| CBH1 | 26.9 | 29.4 | 29.7 | 25.9 | 28.5 | 24.6 | 25.2 | 20.9 | 31.1 |
| CBH2 + EG1 | 25.3 | 26.0 | 26.8 | 25.1 | 25.8 | 25.2 | 25.7 | 25.5 | 24.9 |
| XYN1 + XYN2 | 9.1 | 5.8 | 3.0 | 7.6 | 1.5 | 7.0 | 3.9 | 9.7 | 2.9 |
| others | 36.6 | 37.1 | 39.3 | 38.6 | 41.9 | 41.1 | 42.1 | 40.8 | 39.3 |

As described above, the productivities of not only xylanase but also main cellulase, CBH1, CBH2, and EG1, were drastically improved, compared to XYR1 alone mutation, by combining XYR1 mutation and ACE3 high level expression. The effective mutation of XYR1 is not limited to V821F and A824V, and mutant XYR1 having a mutation of at least one amino acid in a region that is assumed to be an α-helix in the acidic activation domain of XYR1 and showing a glucose blind phenotype (in general, a property of improving the protein productivity even if glucose which causes catabolite repression is used) was effective for production of cellulase and xylanase in the absence of an inducer. Accordingly, it was demonstrated that the combination of XYR1 mutation and ACE3 high level expression activates the promoter of a cellulase/xylanase gene to efficiently induce protein production as in the case of using a cellulase inducer such as cellulose even when a cellulase noninducible carbon source such as glucose is used.

What is claimed is:

1. A method for producing a mutant filamentous fungus, comprising:

modifying Xylanase Regulator 1 (XYR1) and Activator of Cellulase Expression 3 (ACE3) expression in a parent filamentous fungus, wherein the modification of XYR1 is substitution, deletion, insertion, or addition of at least one amino acid residue in a region corresponding to positions 810 to 833 of SEQ ID NO: 1 in a polypeptide that consists of SEQ ID NO: 1 or an amino acid sequence having at least 90% identity thereto and functions as a transcriptional activator of cellulase and hemicellulase, and the modification of ACE3 expression is enhanced expression of a polypeptide that consists of the amino acid sequence at positions 107 to 734 of SEQ ID NO: 3 or an amino acid sequence having at least 90% identity thereto, wherein if the substitution of at least one amino acid residue in XYR1 is a substitution of Ala at a position corresponding to position 824 of SEQ ID NO: 1, the substitution is with Glu, Ile, Leu, Lys, Phe, Thr, Trp, or Tyr, and if the substitution of at least one amino acid residue in XYR is a substitution of Val at a position corresponding to position 821 of SEQ ID NO: 1, the substitution is with Lys, Trp, or Tyr.

2. The method according to claim 1, wherein the at least one amino acid residue is at least one selected from the group consisting of Val, Ala, Thr, and Glu, and the at least one amino acid residue is substituted.

3. The method according to claim 2, wherein the at least one amino acid residue is at least one selected from the group consisting of amino acid residues at positions corresponding to positions 817, 821, 824, 825, and 826 of SEQ ID NO: 1.

4. The method according to claim 2, wherein the at least one amino acid residue is substituted with Val, Glu, Ile, Leu, Lys, Phe, Thr, Trp, or Tyr.

5. The method according to claim 2, wherein the substitution of at least one amino acid is selected from the group consisting of followings:

substitution of Thr at a position corresponding to position 817 of SEQ ID NO: 1 with Tyr;

substitution of Val at a position corresponding to position 821 of SEQ ID NO: 1 with Lys, Trp, or Tyr;

substitution of Ala at a position corresponding to position 824 of SEQ ID NO: 1 with Glu, Ile, Leu, Lys, Phe, Thr, Trp, or Tyr;

substitution of Glu at a position corresponding to position 825 of SEQ ID NO: 1 with Tyr; and substitution of Ala at a position corresponding to position 826 of SEQ ID NO: 1 with Val, Ile, Leu, Phe, Trp, or Tyr.

6. The method according to claim 1, wherein the enhanced expression of a polypeptide is performed by improving a transcription level of a gene coding for the polypeptide.

7. The method according to claim 1, wherein the mutant filamentous fungus expresses cellulase in the absence of a cellulase inducer.

8. The method according to claim 1, wherein the filamentous fungus is a *Trichoderma* fungus.

9. The method according to claim 8, wherein the *Trichoderma* fungus is *Trichoderma reesei*.

10. A method for producing a protein, comprising culturing the mutant filamentous fungus produced by the method according to claim 1.

11. The method according to claim 10, wherein the protein is cellulase, hemicellulase, or a combination of cellulase and hemicellulase.

12. The method according to claim 10, wherein the culture is performed in the presence of glucose.

13. A mutant filamentous fungus comprising modified Xylanase Regulator 1 (XYR1) and showing enhanced expression of a partial polypeptide of Activator of Cellulase Expression 3 (ACE3) compared to a parent filamentous fungus, wherein the modified XYR1 is a polypeptide having a substitution, deletion, insertion or addition of at least one amino acid residue in a region corresponding to positions 810 to 833 of SEQ ID NO: 1 in the amino acid sequence of SEQ ID NO: 1 or an amino acid sequence having at least 90% identity thereto, and the polypeptide functioning as a transcriptional activator of cellulase and hemicellulase, and the partial polypeptide of ACE3 is a polypeptide consisting of the amino acid sequence at positions 107 to 734 of SEQ ID NO: 3 or an amino acid sequence having at least 90% identity thereto, wherein if the substitution of at least one amino acid residue in XYR1 is a substitution of Ala at a position corresponding to position 824 of SEQ ID NO: 1, the substitution is with Glu, Ile, Leu, Lys, Phe, Thr, Trp, or Tyr, and if the substitution of at least one amino acid residue in XYR is a substitution of Val at a position corresponding to position 821 of SEQ ID NO: 1, the substitution is with Lys, Trp, or Tyr.

14. The mutant filamentous fungus according to claim 13, wherein the modified XYR1 is a polypeptide that consists of an amino acid sequence having at least 90% identity to SEQ ID NO: 1 including at least one amino acid residue selected from the group consisting of the following (a) to (m):

(a) Val, Ile, Leu, Phe, Trp, or Tyr at a position corresponding to position 812 of SEQ ID NO: 1;

(b) Phe, Trp, or Tyr at a position corresponding to position 814 of SEQ ID NO: 1;

(c) Val, Ile, Leu, Phe, Trp, or Tyr at a position corresponding to position 816 of SEQ ID NO: 1;

(d) Tyr at a position corresponding to position 817 of SEQ ID NO: 1;

(e) Val, Ile, Leu, Phe, Trp, or Tyr at a position corresponding to position 820 of SEQ ID NO: 1;

(f) Lys, Trp, or Tyr at a position corresponding to position 821 of SEQ ID NO: 1;

(g) Val, Ile, Leu, Phe, Trp, or Tyr at a position corresponding to position 823 of SEQ ID NO: 1;

(h) Glu, Ile, Leu, Lys, Phe, Thr, Trp, or Tyr at a position corresponding to position 824 of SEQ ID NO: 1;

(i) Tyr at a position corresponding to position 825 of SEQ ID NO: 1;

(j) Val, Ile, Leu, Phe, Trp, or Tyr at a position corresponding to position 826 of SEQ ID NO: 1;

(k) Phe, Trp, or Tyr at a position corresponding to position 827 of SEQ ID NO: 1;

(l) Phe, Trp, or Tyr at a position corresponding to position 830 of SEQ ID NO: 1; and (m) Phe, Trp, or Tyr at a position corresponding to position 831 of SEQ ID NO: 1, and the polypeptide functions as a transcriptional activator of cellulase and hemicellulase.

15. The filamentous fungus according to claim 14, wherein the modified XYR1 is a polypeptide that consists of an amino acid sequence having at least 90% identity to SEQ ID NO: 1 including at least one amino acid residue selected from the group consisting of the following:

Lys, Trp, or Tyr at a position corresponding to position 821 of SEQ ID NO: 1; and Glu, Ile, Leu, Lys, Phe, Thr, Trp, or Tyr at a position corresponding to position 824 of SEQ ID NO: 1, and the polypeptide functions as a transcriptional activator of cellulase and hemicellulase.

16. The filamentous fungus according to claim 14, wherein the modified XYR1 is a polypeptide that consists of an amino acid sequence having at least 90% identity to SEQ ID NO: 1 including at least one amino acid residue selected from the group consisting of the following:

Tyr at a position corresponding to position 817 of SEQ ID NO: 1;

Tyr at a position corresponding to position 825 of SEQ ID NO: 1; and

Val, Ile, Leu, Phe, Trp, or Tyr at a position corresponding to position 826 of SEQ ID NO: 1, and the polypeptide functions as a transcriptional activator of cellulase and hemicellulase.

17. The method according to claim 5, wherein the enhanced expression of a polypeptide is performed by improving a transcription level of a gene co ding for the polypeptide.

18. The method according to claim 7, wherein the filamentous fungus is a *Trichoderma* fungus.

19. A method for producing a protein, comprising culturing the mutant filamentous fungus produced by the method according to claim 7.

20. The method according to claim 19, wherein the protein is cellulase, hemicellulase, or a combination of cellulase and hemicellulase.

\* \* \* \* \*

SEQUENCE LISTING

<160> NUMBER OF SEQ ID NOS: 51

<210> SEQ ID NO 1
<211> LENGTH: 940

-continued

```
<212> TYPE: PRT
<213> ORGANISM: Trichoderma reesei

<400> SEQUENCE: 1

Met Leu Ser Asn Pro Leu Arg Arg Tyr Ser Ala Tyr Pro Asp Ile Ser
1               5                   10                  15

Ser Ala Ser Phe Asp Pro Asn Tyr His Gly Ser Gln Ser His Leu His
                20                  25                  30

Ser Ile Asn Val Asn Thr Phe Gly Asn Ser His Pro Tyr Pro Met Gln
            35                  40                  45

His Leu Ala Gln His Ala Glu Leu Ser Ser Ser Arg Met Ile Arg Ala
        50                  55                  60

Ser Pro Val Gln Pro Lys Gln Arg Gln Gly Ser Leu Ile Ala Ala Arg
65                  70                  75                  80

Lys Asn Ser Thr Gly Thr Ala Gly Pro Ile Arg Arg Arg Ile Ser Arg
                85                  90                  95

Ala Cys Asp Gln Cys Asn Gln Leu Arg Thr Lys Cys Asp Gly Leu His
            100                 105                 110

Pro Cys Ala His Cys Ile Glu Phe Gly Leu Gly Cys Glu Tyr Val Arg
        115                 120                 125

Glu Arg Lys Lys Arg Gly Lys Ala Ser Arg Lys Asp Ile Ala Ala Gln
        130                 135                 140

Gln Ala Ala Ala Ala Ala Ala Gln His Ser Gly Gln Val Gln Asp Gly
145                 150                 155                 160

Pro Glu Asp Gln His Arg Lys Leu Ser Arg Gln Gln Ser Glu Ser Ser
                165                 170                 175

Arg Gly Ser Ala Glu Leu Ala Gln Pro Ala His Asp Pro Pro His Gly
            180                 185                 190

His Ile Glu Gly Ser Val Ser Ser Phe Ser Asp Asn Gly Leu Ser Gln
            195                 200                 205

His Ala Ala Met Gly Gly Met Asp Gly Leu Glu Asp His His Gly His
        210                 215                 220

Val Gly Val Asp Pro Ala Leu Gly Arg Thr Gln Leu Glu Ala Ser Ser
225                 230                 235                 240

Ala Met Gly Leu Gly Ala Tyr Gly Glu Val His Pro Gly Tyr Glu Ser
                245                 250                 255

Pro Gly Met Asn Gly His Val Met Val Pro Pro Ser Tyr Gly Ala Gln
                260                 265                 270

Thr Thr Met Ala Gly Tyr Ser Gly Ile Ser Tyr Ala Ala Gln Ala Pro
        275                 280                 285

Ser Pro Ala Thr Tyr Ser Ser Asp Gly Asn Phe Arg Leu Thr Gly His
        290                 295                 300

Ile His Asp Tyr Pro Leu Ala Asn Gly Ser Ser Pro Ser Trp Gly Val
305                 310                 315                 320

Ser Leu Ala Ser Pro Ser Asn Gln Phe Gln Leu Gln Leu Ser Gln Pro
                325                 330                 335

Ile Phe Lys Gln Ser Asp Leu Arg Tyr Pro Val Leu Glu Pro Leu Leu
            340                 345                 350

Pro His Leu Gly Asn Ile Leu Pro Val Ser Leu Ala Cys Asp Leu Ile
        355                 360                 365

Asp Leu Tyr Phe Ser Ser Ser Ser Ala Gln Met His Pro Met Ser
        370                 375                 380

Pro Tyr Val Leu Gly Phe Val Phe Arg Lys Arg Ser Phe Leu His Pro
385                 390                 395                 400
```

-continued

```
Thr Asn Pro Arg Arg Cys Gln Pro Ala Leu Leu Ala Ser Met Leu Trp
            405             410             415

Val Ala Ala Gln Thr Ser Glu Ala Ser Phe Leu Thr Ser Leu Pro Ser
            420             425             430

Ala Arg Ser Lys Val Cys Gln Lys Leu Leu Glu Leu Thr Val Gly Leu
            435             440             445

Leu Gln Pro Leu Ile His Thr Gly Thr Asn Ser Pro Ser Pro Lys Thr
    450             455             460

Ser Pro Val Val Gly Ala Ala Ala Leu Gly Val Leu Gly Val Ala Met
465             470             475             480

Pro Gly Ser Leu Asn Met Asp Ser Leu Ala Gly Glu Thr Gly Ala Phe
            485             490             495

Gly Ala Ile Gly Ser Leu Asp Asp Val Ile Thr Tyr Val His Leu Ala
            500             505             510

Thr Val Val Ser Ala Ser Glu Tyr Lys Gly Ala Ser Leu Arg Trp Trp
            515             520             525

Gly Ala Ala Trp Ser Leu Ala Arg Glu Leu Lys Leu Gly Arg Glu Leu
    530             535             540

Pro Pro Gly Asn Pro Pro Ala Asn Gln Glu Asp Gly Glu Gly Leu Ser
545             550             555             560

Glu Asp Val Asp Glu His Asp Leu Asn Arg Asn Asn Thr Arg Phe Val
            565             570             575

Thr Glu Glu Glu Arg Glu Glu Arg Arg Arg Ala Trp Trp Leu Val Tyr
            580             585             590

Ile Val Asp Arg His Leu Ala Leu Cys Tyr Asn Arg Pro Leu Phe Leu
            595             600             605

Leu Asp Ser Glu Cys Ser Asp Leu Tyr His Pro Met Asp Asp Ile Lys
    610             615             620

Trp Gln Ala Gly Lys Phe Arg Ser His Asp Ala Gly Asn Ser Ser Ile
625             630             635             640

Asn Ile Asp Ser Ser Met Thr Asp Glu Phe Gly Asp Ser Pro Arg Ala
            645             650             655

Ala Arg Gly Ala His Tyr Glu Cys Arg Gly Arg Ser Ile Phe Gly Tyr
            660             665             670

Phe Leu Ser Leu Met Thr Ile Leu Gly Glu Ile Val Asp Val His His
            675             680             685

Ala Lys Ser His Pro Arg Phe Gly Val Gly Phe Arg Ser Ala Arg Asp
    690             695             700

Trp Asp Glu Gln Val Ala Glu Ile Thr Arg His Leu Asp Met Tyr Glu
705             710             715             720

Glu Ser Leu Lys Arg Phe Val Ala Lys His Leu Pro Leu Ser Ser Lys
            725             730             735

Asp Lys Glu Gln His Glu Met His Asp Ser Gly Ala Val Thr Asp Met
            740             745             750

Gln Ser Pro Leu Ser Val Arg Thr Asn Ala Ser Ser Arg Met Thr Glu
            755             760             765

Ser Glu Ile Gln Ala Ser Ile Val Val Ala Tyr Ser Thr His Val Met
    770             775             780

His Val Leu His Ile Leu Leu Ala Asp Lys Trp Asp Pro Ile Asn Leu
785             790             795             800

Leu Asp Asp Asp Asp Leu Trp Ile Ser Ser Glu Gly Phe Val Thr Ala
            805             810             815
```

-continued

```
Thr Ser His Ala Val Ser Ala Ala Glu Ala Ile Ser Gln Ile Leu Glu
            820                 825                 830

Phe Asp Pro Gly Leu Glu Phe Met Pro Phe Phe Tyr Gly Val Tyr Leu
            835                 840                 845

Leu Gln Gly Ser Phe Leu Leu Leu Leu Ile Ala Asp Lys Leu Gln Ala
            850                 855                 860

Glu Ala Ser Pro Ser Val Ile Lys Ala Cys Glu Thr Ile Val Arg Ala
865                 870                 875                 880

His Glu Ala Cys Val Val Thr Leu Ser Thr Glu Tyr Gln Arg Asn Phe
                885                 890                 895

Ser Lys Val Met Arg Ser Ala Leu Ala Leu Ile Arg Gly Arg Val Pro
            900                 905                 910

Glu Asp Leu Ala Glu Gln Gln Gln Arg Arg Arg Glu Leu Leu Ala Leu
            915                 920                 925

Tyr Arg Trp Thr Gly Asn Gly Thr Gly Leu Ala Leu
    930                 935                 940
```

```
<210> SEQ ID NO 2
<211> LENGTH: 2950
<212> TYPE: DNA
<213> ORGANISM: Trichoderma reesei

<400> SEQUENCE: 2
atgttgtcca atcctctccg tcgctattct gcctaccccg acatctcctc ggcgtcattt       60
gacccgaact accatggctc acagtcgcat ctccactcga tcaacgtcaa cacattcggc      120
aacagccacc cctatcccat gcagcacctc gcacagcatg cggagctttc gagttcacgc      180
atgataaggg ccagtccggt gcagccaaag cagcgccagg gctctcttat tgctgccagg      240
aagaattcaa cgggtactgc tgggcccatt cggcggagga tcagtcgcgc ttgtgaccag      300
tgcaaccagc ttcgtaccaa gtgcgatggc ttacacccat gtgcccattg tataggtatg      360 tccctttttcc tctacacagt gatgctgcgc tcaagcacat gtactgatcg atcttgttta      420
gaattcggcc ttggatgcga atatgtccga gagagaaaga agcgtggcaa agcttcgcgc      480
aaggatattg ctgcccagca agccgcggcg gctgcagcac aacactccgg ccaggtccag      540
gatggtccag aggatcaaca tcgcaaactc tcacgccagc aaagcgaatc ttcgcgtggc      600
agcgctgagc ttgcccagcc tgcccacgac ccgcctcatg gccacattga gggctctgtc      660
agctccttca gcgacaatgg cctttcccag catgctgcca tgggcggcat ggatggcctg      720
gaagatcacc atggccacgt cggagttgat cctgccctgg gccgaactca gctggaagcg      780
tcatcagcaa tgggcctggg cgcatacggt gaagtccacc ccggctatga gagccccggc      840
atgaatggcc atgtgatggt gccccgtcg tatggcgcgc agaccaccat ggccgggtat      900
tccggtatct cgtatgctgc gcaagccccg agtccggcta cgtatagcag cgacggtaac      960
tttcgactca ccggtcacat ccatgattac ccgctggcaa atgggagctc gccctcatgg     1020
ggagtctcgc tggcctcgcc ttcgaaccag ttccagcttc agctctcgca gcccatcttc     1080
aagcaaagcg atttgcgata tcctgtgctt gagcctctgc tgcctcacct gggaaacatc     1140
ctccccgtgt ctttggcgtg cgatctgatt gacctgtact tctcctcgtc ttcatcagca     1200
cagatgcacc caatgtcccc atacgttctg ggcttcgtct ccggaagcg ctccttcttg     1260 cacccccacga acccacgaag gtgccagccc gcgctgcttg cgagcatgct gtgggtggcg     1320
gcacagacta gcgaagcgtc cttcttgacg agcctgccgt cggcgaggag caaggtctgc     1380
cagaagctgc tcgagctgac cgttgggctt cttcagcccc tgatccacac cggcaccaac     1440
```

-continued

```
agcccgtctc ccaagactag ccccgtcgtc ggtgctgctg ccctgggagt tcttggggtg    1500
gccatgccgg gctcgctgaa catggattca ctggccggcg aaacgggtgc ttttggggcc    1560
atagggagcc ttgacgacgt catcacctat gtgcacctcg ccacggtcgt ctcggccagc    1620
gagtacaagg gcgccagcct gcggtggtgg ggtgcggcat ggtctctcgc cagagagctc    1680
aagcttggcc gtgagctgcc gcctggcaat ccacctgcca accaggagga cggcgagggc    1740
cttagcgaag acgtggatga gcacgacttg aacagaaaca acactcgctt cgtgacggaa    1800
gaggagcgcg aagagcgacg gcgagcatgg tggctcgttt acatcgtcga caggcacctg    1860
gcgctctgct acaaccgccc cttgtttctt ctggacagcg agtgcagcga cttgtaccac    1920
ccgatggacg acatcaagtg gcaggcaggc aaatttcgca gccacgatgc agggaactcc    1980
agcatcaaca tcgatagctc catgacggac gagtttggcg atagtccccg ggcggctcgc    2040
ggcgcacact acgagtgccg cggtcgtagc attttttggct acttcttgtc cttgatgaca    2100
atcctgggcg agattgtcga tgtccaccat gctaaaagcc accccggtt cggcgttgga    2160 ttccgctccg cgcgggattg ggacgagcag gttgctgaaa tcacccgaca cctggacatg    2220
tatgaggaga gcctcaagag gttcgtggcc aagcatctgc cattgtcctc aaaggacaag    2280
gagcagcatg agatgcacga cagtggagcg gtaacagaca tgcaatctcc actctcggtg    2340
cggaccaacg cgtccagccg catgacggag agcgagatcc aggccagcat cgtggtggct    2400
tacagcaccc atgtgatgca tgtcctccac atcctccttg cggataagtg ggatcccatc    2460
aaccttctag acgacgacga cttgtggatc tcgtcggaag gattcgtgac ggcgacgagc    2520
cacgcggtat cggctgccga agctattagc cagattctcg agtttgaccc tggcctggag    2580
tttatgccat tcttctacgg cgtctatctc ctgcagggtt ccttcctcct cctgctcatc    2640
gccgacaagc tgcaggccga agcgtctcca agcgtcatca aggcttgcga gaccattgtt    2700
agggcacacg aagcttgcgt tgtgacgctg agcacagagt atcaggtaag ccctatcagt    2760
tcaaacgtct atcttgctgt gaatcaaaga ctgacttgga catcagcgca actttagcaa    2820
ggttatgcga agcgcgctgg ctctgattcg gggccgtgtg ccggaagatt tagctgagca    2880
gcagcagcga cgacgcgagc ttcttgcact ataccgatgg actggtaacg gaaccggtct    2940
ggccctctaa                                                           2950
```

<210> SEQ ID NO 3
<211> LENGTH: 734
<212> TYPE: PRT
<213> ORGANISM: Trichoderma reesei

<400> SEQUENCE: 3

```
Met Ala Thr Ala Ala Ala Ala Ala Ala Gly Gly Ala Ala Val Ala Ala
1               5                   10                  15

Gly Ala Asp Thr Gly Ala Ala Gly Ser Ser Ser Thr Gly Pro Pro Gly
            20                  25                  30

Leu Pro Gly Leu Pro Gly Thr Arg Thr Gly Ser Val Ala Met Gly Ser
        35                  40                  45

Ala Ala Pro Ala Gln Gly Ser Val Ala Ala Ala Gly Gly Pro Pro
    50                  55                  60

Ala Ala Gly Ala Gly Ala Gly Ala Val His Ala Leu Thr Thr Ser Pro
65                  70                  75                  80

Glu Ser Ala Ser Ala Ser Gln Pro Gly Ser Pro Thr Ala Ser Thr Thr
            85                  90                  95
```

-continued

```
Pro Pro Gln Asn Ser Leu Val Ser Ala Ala Thr Ser Phe His His His
        100             105             110

Pro Arg Gly Arg Leu Val Ser Arg Ala Cys Asp Arg Cys Arg Arg
        115             120             125

Lys Ala Lys Cys Glu Tyr Leu Ser Ala Val Asp Ser Cys Thr His Cys
        130             135             140

Arg Asp Ala His Val Gln Cys Thr Phe Asp Leu Pro Leu Ala Arg Arg
145             150             155             160

Gly Pro Lys Ala Arg Lys Lys Ser Asp Gln Pro Gly Gln Pro Pro Pro
                165             170             175

Asp Pro Ser Ser Leu Ser Thr Ala Ala Arg Pro Gly Gln Met Pro Pro
            180             185             190

Pro Leu Thr Phe Ser Gly Pro Ala Val Ala Ala Leu Gln Pro Phe Ala
            195             200             205

Ser Ser Ser Leu Ser Pro Asp Ala Ala Trp Glu Pro Val Glu Pro Leu
        210             215             220

Ser Ile Asp Asn Gly Leu Pro Arg Gln Pro Leu Gly Asp Leu Pro Gly
225             230             235             240

Leu Ser Thr Ile Gln Asn Ile Ser Thr Arg Gln Arg Trp Ile His Leu
                245             250             255

Ala Asn Ala Met Thr Leu Arg Asn Thr Thr Leu Glu Arg Val Ser Lys
            260             265             270

Arg Cys Ile Asp Leu Phe Phe Asp Tyr Leu Tyr Pro Leu Thr Pro Leu
            275             280             285

Val Tyr Glu Pro Ala Leu Arg Asp Val Leu Ala Tyr Ile Phe Ser Gln
        290             295             300

Pro Leu Pro Gly Val Asn Gln Pro Ser Pro Leu Ser Gln Leu Thr Pro
305             310             315             320

Asp Pro Thr Thr Gly Thr Thr Pro Leu Asn Ala Ala Glu Ser Trp Ala
                325             330             335

Gly Phe Gly Gln Pro Ser Gly Ser Arg Thr Val Gly Ser Arg Leu Ala
            340             345             350

Pro Trp Ala Asp Ser Thr Phe Thr Leu Val Thr Ala Val Cys Ala Glu
            355             360             365

Ala Ala Phe Met Leu Pro Lys Asp Ile Phe Pro Glu Gly Glu Ser Val
        370             375             380

Ser Glu Ile Leu Leu Glu Ala Ser Arg Asp Cys Leu His Gln His Leu
385             390             395             400

Glu Ala Asp Leu Glu Asn Pro Thr Ala Asn Ser Ile Ala Ile Arg Tyr
                405             410             415

Phe His Ser Asn Cys Leu His Ala Ala Gly Lys Pro Lys Tyr Ser Trp
            420             425             430

His Ile Phe Gly Glu Ala Ile Arg Leu Ala Gln Val Met Gln Leu His
            435             440             445

Glu Glu Ala Ala Leu Glu Gly Leu Val Pro Ile Glu Ala Glu Phe Arg
        450             455             460

Arg Arg Cys Phe Trp Ile Leu Tyr Leu Gly Asp Lys Ser Ala Ala Ile
465             470             475             480

Leu Asn Asn Arg Pro Ile Thr Ile His Lys Tyr Cys Phe Asp Ala Gly
                485             490             495

Ile Thr Thr Leu Tyr Pro Ser Gly Ile Glu Asp Glu Phe Leu Ser Thr
            500             505             510

Ala Ser Glu Pro Pro Arg Lys Ser Phe Ile Ser Gly Phe Asn Ala Asn
```

-continued

```
            515                 520                 525
Val Arg Leu Trp Gln Ser Ala Ala Asp Leu Leu Leu Glu Ile Arg Val
    530                 535                 540

Leu Gln Asp Gln Met Met Gln His Phe Arg Gly Thr Met Pro Pro Asn
545                 550                 555                 560

His Val Leu Pro Ser Ala Asp Arg Gln His Leu Asp Ser Leu Tyr Val
                565                 570                 575

Arg Phe Ile Thr Cys Leu Asp Asp Leu Pro Pro Tyr Leu Gln Ser Cys
                580                 585                 590

Thr Leu Ala Met Ala Ala Met Ala Glu Gly Asn Gly Ser Ala Glu Ser
            595                 600                 605

Lys Gln Tyr Val Ile Gln Cys Ile Asn Leu Gln Val Thr Phe His Cys
        610                 615                 620

Leu Arg Met Val Ile Thr Gln Lys Phe Glu Asp Leu Ser Tyr Phe Ala
625                 630                 635                 640

Pro Gly Val Glu Gln Ala Asp Leu Arg Lys Ser Glu Ile Val Arg Asp
                645                 650                 655

Met Leu Arg Val Met Asn Glu Ala Pro Phe Trp Gly Leu Gln Ala Asn
            660                 665                 670

Gly Glu Pro Asn Val Glu Lys Ile Arg Leu Ile Gly Ala Ser Leu Leu
            675                 680                 685

Ala Ile Ile His Arg Asn Gln Asp Ser Pro Leu Ala Thr Arg Ala Arg
    690                 695                 700

Ser Asp Phe Ser Val Leu Leu Asp Ile Leu Thr Arg Leu Asp Ser Lys
705                 710                 715                 720

Ala Ser Asp Gln Leu Arg Asn Thr Ser Thr Thr Val Val Gly
                725                 730

<210> SEQ ID NO 4
<211> LENGTH: 2918
<212> TYPE: DNA
<213> ORGANISM: Trichoderma reesei

<400> SEQUENCE: 4
atggccacag cggccgcggc agcagctggc ggcgcggcgg ttgctgcggg tgcagacaca         60
ggtgcgttga gtcccgtccc gtccgctcgc gttcctcccc agctgccagc ccgcgtgggt        120
ggcactggaa cgcagtgcag cgcaatcagt gcagtgcggc cccccaact aacgctgccc        180 cccgtggctc ctcggccaca caggcgctgc aggctccagc tctacaggcc ctccaggcct        240
tccaggcctt ccaggcaccc ggacaggctc cgtggcgatg ggctcagcag ctccggccca        300
gggctctgta gctgcagctg caggcggccc tccagctgct ggcgctggcg ctggcgctgt        360
ccacgccctc accacctcgc ccgagtctgc ctcggcctcg cagcccggct cgccaaccgc        420
ctcaaccacg ccgccgcaga actcactcgt gtcggctgca acctcgttcc accaccatcc        480
cagaggccgt ctggtgagca gagcctgcga ccgctgccgc cggcgcaagg ccaaggtcag        540
tctagcccct ttgctgttgc ttgcatctct gttgtcattg ctcctcctcc tgctgctgct        600
gatgctgctg ctcctcctcc tcctcctcct ccccgtctcc tggtccctgg tccctgctct        660
tcatatgtcc ttactgcccg tgtctcctct ccccgttccc gttcccctc ctcccgtcct        720 cttctcctgc gtgtctgtca tgcgtacaaa gcatacatac aatacatcag catacatggc        780
aagcgttgtg ttgtgttgag agttgtgtgt attgtattgc actgccttca caactcgttc        840
atactgctgc agcctcaccc caacaccgac ctcgtcttcc atgctgcgct actcccccgt        900
```

-continued

```
cttacacctg gatactctct ccttgccacc actgaccaat gctcttcccc gcccaaagtg        960
cgagtacctc agcgctgtcg atagctgcac gcactgccgc gatgcccacg tgcagtgcac       1020
tttcgacctg ccctggcgc gacgcggccc caaagcgagg aagaagagcg accagcccgg       1080
ccagccgcct cctgatccga gctcgctctc caccgcggct cgacccggcc agatgccgcc       1140
gccgctgacc ttctccggcc ccgcagtagc cgcgctgcag cccttcgcct cgtcgtcgct       1200
gtcgcccgac gcggcctggg agcccgtcga gccgctcagc attgacaacg gcctgccccg       1260
gcagccgctg ggcgacctgc ccggcctctc caccatccag aacatctcga cgcgccagcg       1320
atggatacac ctggccaacg ccatgacgct gcgcaacacg acgctagagc gcgtctcgaa       1380
gcgatgtatc gacctcttct tcgactacct ctacccctc accccctgg tgtacgagcc        1440 ggccctccgg gacgtgctcg catacatctt ctcccagccc ttgcctggcg tcaaccaacc       1500
atcgccgctg tcacagctca cgccagaccc gaccaccggc accacccccc tcaacgctgc       1560
cgagtcgtgg gccggctttg gccagcccag cggctcgcga accgtcggca gcaggctggc       1620
tccctgggcc gactcgacct tcaccctggt cacggccgtc tgcgcagagg cagcattcat       1680
gctacccaag gacattttcc ccgaaggaga atccgtctct gagatcttgc tcgaagcctc       1740
tcgggactgc ctgcaccagc acctcgaggc cgacctggag aatccgacgg ccaactcgat       1800
tgccattcgc tacttccact ccaactgcct ccacgctgcg gggaagccca agtactcgtg       1860
gcacatattt ggcgaggcca tccgcctggc gcaggtcatg cagctgcacg aggaggctgc       1920
cctcgagggg ctcgtcccca tcgaggcaga gttccgccgt cgctgctttt ggatcctgta       1980
cttgggcgac aagtcagccg ctatactcaa caatcggccc atcaccatcc acaagtactg       2040
cttcgacgcc ggcatcacca cgctataccc gtcgggtatc gaggacgagt tcctgagcac       2100
ggcgtccgag ccgccccgga agagcttcat atccggcttc aacgcaaatg tgcggctctg       2160
gcagtccgcg gctgatttgc tgctggaaat ccgcgtgctg caagatcaga tgatgcagca       2220
ctttcgaggg accatgcccc cgaaccatgt gctgccctcc gccgacaggc agcatctcga       2280
ttctctctat gtccgcttca tcacctgctt ggacgatctc ccgccgtacc tccagtcgtg       2340
cactctggcg atggcagcga tggcagaagg caacgggtct gccgagtcca agcagtacgt       2400
gatacagtgc atcaacctgc aggtgacgtt tcactgtctg cgcatggtaa ttacgcagaa       2460
attcgaagac ctctcttatt ttgctcctgg cgttgagcag gctgatctca gaaagtcgga       2520
gattgtgcga gacatgctga gggtgatgaa cgaggcgccc ttttggggcc tgcaggccaa       2580
tggcgagcca aacgtgagtc gtttccttgt ctcttctctt ttctgcacac ccttttcttc       2640
gacgaccccc cctctctctt tatatccctg cggatatgta tatcatcaag cctcggcact       2700
tgttgctaat ctgtcctgat tatgttgtct ggatgctgca ggttgaaaag attcgcctta       2760
tcggagctag tttgctggcc atcatccatc gcaaccagga ttcacccttg gctacgcgag       2820
ccaggagcga ctttttccgtg cttttggata ttctcacgcg gctggactcg aaggcgtcgg       2880
accaactgag gaatacgtcc actaccgttg ttggctaa                               2918
```

<210> SEQ ID NO 5
<211> LENGTH: 20
<212> TYPE: DNA
<213> ORGANISM: Artificial
<220> FEATURE:
<223> OTHER INFORMATION: Oligonucleotide primer
<400> SEQUENCE: 5

```
acggggtacg cgtgaaattg                                                     20
```

```
<210> SEQ ID NO 6
<211> LENGTH: 20
<212> TYPE: DNA
<213> ORGANISM: Artificial
<220> FEATURE:
<223> OTHER INFORMATION: Oligonucleotide primer

<400> SEQUENCE: 6
tgtgactgat taatgtatga                                                20

<210> SEQ ID NO 7
<211> LENGTH: 35
<212> TYPE: DNA
<213> ORGANISM: Artificial
<220> FEATURE:
<223> OTHER INFORMATION: Oligonucleotide primer

<400> SEQUENCE: 7
cattaatcag tcacaatgtt gtccaatcct ctccg                              35

<210> SEQ ID NO 8
<211> LENGTH: 35
<212> TYPE: DNA
<213> ORGANISM: Artificial
<220> FEATURE:
<223> OTHER INFORMATION: Oligonucleotide primer

<400> SEQUENCE: 8
tttcgccacg gagctttaga gggccagacc ggttc                              35

<210> SEQ ID NO 9
<211> LENGTH: 35
<212> TYPE: DNA
<213> ORGANISM: Artificial
<220> FEATURE:
<223> OTHER INFORMATION: Oligonucleotide primer

<400> SEQUENCE: 9
cattaatcag tcacaatgct gcgctactcc cccgt                              35

<210> SEQ ID NO 10
<211> LENGTH: 35
<212> TYPE: DNA
<213> ORGANISM: Artificial
<220> FEATURE:
<223> OTHER INFORMATION: Oligonucleotide primer

<400> SEQUENCE: 10
tttcgccacg gagctttagc caacaacggt agtgg                              35

<210> SEQ ID NO 11
<211> LENGTH: 20
<212> TYPE: DNA
<213> ORGANISM: Artificial
<220> FEATURE:
<223> OTHER INFORMATION: Oligonucleotide primer

<400> SEQUENCE: 11
agctccgtgg cgaaagcctg                                               20

<210> SEQ ID NO 12
<211> LENGTH: 20
<212> TYPE: DNA
<213> ORGANISM: Artificial
<220> FEATURE:
```

-continued

<223> OTHER INFORMATION: Oligonucleotide primer

<400> SEQUENCE: 12
ctcggctacg ttgtcatcgt                                                    20

<210> SEQ ID NO 13
<211> LENGTH: 20
<212> TYPE: DNA
<213> ORGANISM: Artificial
<220> FEATURE:
<223> OTHER INFORMATION: Oligonucleotide primer

<400> SEQUENCE: 13
caaaccagcc aaggtaggta                                                    20

<210> SEQ ID NO 14
<211> LENGTH: 20
<212> TYPE: DNA
<213> ORGANISM: Artificial
<220> FEATURE:
<223> OTHER INFORMATION: Oligonucleotide primer

<400> SEQUENCE: 14
ttggttcttg gtttggaggg                                                    20

<210> SEQ ID NO 15
<211> LENGTH: 35
<212> TYPE: DNA
<213> ORGANISM: Artificial
<220> FEATURE:
<223> OTHER INFORMATION: Oligonucleotide primer

<400> SEQUENCE: 15
gacaacgtag ccgagaagta ccgcgcgctt gacaa                                   35

<210> SEQ ID NO 16
<211> LENGTH: 35
<212> TYPE: DNA
<213> ORGANISM: Artificial
<220> FEATURE:
<223> OTHER INFORMATION: Oligonucleotide primer

<400> SEQUENCE: 16
accttggctg gtttgctgaa tgcccggtgg taagc                                   35

<210> SEQ ID NO 17
<211> LENGTH: 20
<212> TYPE: DNA
<213> ORGANISM: Artificial
<220> FEATURE:
<223> OTHER INFORMATION: Oligonucleotide primer

<400> SEQUENCE: 17
aagtaccgcg cgcttgacaa                                                    20

<210> SEQ ID NO 18
<211> LENGTH: 20
<212> TYPE: DNA
<213> ORGANISM: Artificial
<220> FEATURE:
<223> OTHER INFORMATION: Oligonucleotide primer

<400> SEQUENCE: 18
ttggttcttg gtttggaggg                                                    20

-continued

```
<210> SEQ ID NO 19
<211> LENGTH: 27
<212> TYPE: DNA
<213> ORGANISM: Artificial
<220> FEATURE:
<223> OTHER INFORMATION: Oligonucleotide primer

<400> SEQUENCE: 19
cacgcgttct cggctgccga agctatt                                    27

<210> SEQ ID NO 20
<211> LENGTH: 27
<212> TYPE: DNA
<213> ORGANISM: Artificial
<220> FEATURE:
<223> OTHER INFORMATION: Oligonucleotide primer

<400> SEQUENCE: 20
agccgagaac gcgtggctcg tcgccgt                                    27

<210> SEQ ID NO 21
<211> LENGTH: 27
<212> TYPE: DNA
<213> ORGANISM: Artificial
<220> FEATURE:
<223> OTHER INFORMATION: Oligonucleotide primer

<400> SEQUENCE: 21
tcggctgtcg aagctattag ccagatt                                    27

<210> SEQ ID NO 22
<211> LENGTH: 27
<212> TYPE: DNA
<213> ORGANISM: Artificial
<220> FEATURE:
<223> OTHER INFORMATION: Oligonucleotide primer

<400> SEQUENCE: 22
agcttcgaca gccgataccg cgtggct                                    27

<210> SEQ ID NO 23
<211> LENGTH: 27
<212> TYPE: DNA
<213> ORGANISM: Artificial
<220> FEATURE:
<223> OTHER INFORMATION: Oligonucleotide primer

<400> SEQUENCE: 23
acggcgtaca gccacgcggt atcggct                                    27

<210> SEQ ID NO 24
<211> LENGTH: 27
<212> TYPE: DNA
<213> ORGANISM: Artificial
<220> FEATURE:
<223> OTHER INFORMATION: Oligonucleotide primer

<400> SEQUENCE: 24
gtggctgtac gccgtcacga atccttc                                    27

<210> SEQ ID NO 25
<211> LENGTH: 27
<212> TYPE: DNA
<213> ORGANISM: Artificial
<220> FEATURE:
<223> OTHER INFORMATION: Oligonucleotide primer
```

-continued

<400> SEQUENCE: 25
cacgcgtact cggctgccga agctatt                                           27

<210> SEQ ID NO 26
<211> LENGTH: 27
<212> TYPE: DNA
<213> ORGANISM: Artificial
<220> FEATURE:
<223> OTHER INFORMATION: Oligonucleotide primer

<400> SEQUENCE: 26
agccgagtac gcgtggctcg tcgccgt                                           27

<210> SEQ ID NO 27
<211> LENGTH: 27
<212> TYPE: DNA
<213> ORGANISM: Artificial
<220> FEATURE:
<223> OTHER INFORMATION: Oligonucleotide primer

<400> SEQUENCE: 27
cacgcgaagt cggctgccga agctatt                                           27

<210> SEQ ID NO 28
<211> LENGTH: 27
<212> TYPE: DNA
<213> ORGANISM: Artificial
<220> FEATURE:
<223> OTHER INFORMATION: Oligonucleotide primer

<400> SEQUENCE: 28
agccgacttc gcgtggctcg tcgccgt                                           27

<210> SEQ ID NO 29
<211> LENGTH: 27
<212> TYPE: DNA
<213> ORGANISM: Artificial
<220> FEATURE:
<223> OTHER INFORMATION: Oligonucleotide primer

<400> SEQUENCE: 29
tcggctatcg aagctattag ccagatt                                           27

<210> SEQ ID NO 30
<211> LENGTH: 27
<212> TYPE: DNA
<213> ORGANISM: Artificial
<220> FEATURE:
<223> OTHER INFORMATION: Oligonucleotide primer

<400> SEQUENCE: 30
agcttcgata gccgataccg cgtggct                                           27

<210> SEQ ID NO 31
<211> LENGTH: 27
<212> TYPE: DNA
<213> ORGANISM: Artificial
<220> FEATURE:
<223> OTHER INFORMATION: Oligonucleotide primer

<400> SEQUENCE: 31
tcggctctcg aagctattag ccagatt                                           27

<210> SEQ ID NO 32
<211> LENGTH: 27

```
<212> TYPE: DNA
<213> ORGANISM: Artificial
<220> FEATURE:
<223> OTHER INFORMATION: Oligonucleotide primer

<400> SEQUENCE: 32
agcttcgaga gccgataccg cgtggct                                          27

<210> SEQ ID NO 33
<211> LENGTH: 27
<212> TYPE: DNA
<213> ORGANISM: Artificial
<220> FEATURE:
<223> OTHER INFORMATION: Oligonucleotide primer

<400> SEQUENCE: 33
tcggctttcg aagctattag ccagatt                                          27

<210> SEQ ID NO 34
<211> LENGTH: 27
<212> TYPE: DNA
<213> ORGANISM: Artificial
<220> FEATURE:
<223> OTHER INFORMATION: Oligonucleotide primer

<400> SEQUENCE: 34
agcttcgaaa gccgataccg cgtggct                                          27

<210> SEQ ID NO 35
<211> LENGTH: 27
<212> TYPE: DNA
<213> ORGANISM: Artificial
<220> FEATURE:
<223> OTHER INFORMATION: Oligonucleotide primer

<400> SEQUENCE: 35
tcggcttggg aagctattag ccagatt                                          27

<210> SEQ ID NO 36
<211> LENGTH: 27
<212> TYPE: DNA
<213> ORGANISM: Artificial
<220> FEATURE:
<223> OTHER INFORMATION: Oligonucleotide primer

<400> SEQUENCE: 36
agcttcccaa gccgataccg cgtggct                                          27

<210> SEQ ID NO 37
<211> LENGTH: 27
<212> TYPE: DNA
<213> ORGANISM: Artificial
<220> FEATURE:
<223> OTHER INFORMATION: Oligonucleotide primer

<400> SEQUENCE: 37
tcggcttacg aagctattag ccagatt                                          27

<210> SEQ ID NO 38
<211> LENGTH: 27
<212> TYPE: DNA
<213> ORGANISM: Artificial
<220> FEATURE:
<223> OTHER INFORMATION: Oligonucleotide primer

<400> SEQUENCE: 38
```

-continued

```
agcttcgtaa gccgataccg cgtggct                                27

<210> SEQ ID NO 39
<211> LENGTH: 27
<212> TYPE: DNA
<213> ORGANISM: Artificial
<220> FEATURE:
<223> OTHER INFORMATION: Oligonucleotide primer

<400> SEQUENCE: 39
tcggctaccg aagctattag ccagatt                                27

<210> SEQ ID NO 40
<211> LENGTH: 27
<212> TYPE: DNA
<213> ORGANISM: Artificial
<220> FEATURE:
<223> OTHER INFORMATION: Oligonucleotide primer

<400> SEQUENCE: 40
agcttcggta gccgataccg cgtggct                                27

<210> SEQ ID NO 41
<211> LENGTH: 27
<212> TYPE: DNA
<213> ORGANISM: Artificial
<220> FEATURE:
<223> OTHER INFORMATION: Oligonucleotide primer

<400> SEQUENCE: 41
tcggctaagg aagctattag ccagatt                                27

<210> SEQ ID NO 42
<211> LENGTH: 27
<212> TYPE: DNA
<213> ORGANISM: Artificial
<220> FEATURE:
<223> OTHER INFORMATION: Oligonucleotide primer

<400> SEQUENCE: 42
agcttcctta gccgataccg cgtggct                                27

<210> SEQ ID NO 43
<211> LENGTH: 27
<212> TYPE: DNA
<213> ORGANISM: Artificial
<220> FEATURE:
<223> OTHER INFORMATION: Oligonucleotide primer

<400> SEQUENCE: 43
tcggctgagg aagctattag ccagatt                                27

<210> SEQ ID NO 44
<211> LENGTH: 27
<212> TYPE: DNA
<213> ORGANISM: Artificial
<220> FEATURE:
<223> OTHER INFORMATION: Oligonucleotide primer

<400> SEQUENCE: 44
agcttcctca gccgataccg cgtggct                                27

<210> SEQ ID NO 45
<211> LENGTH: 27
<212> TYPE: DNA
<213> ORGANISM: Artificial
```

-continued

<220> FEATURE:
<223> OTHER INFORMATION: Oligonucleotide primer

<400> SEQUENCE: 45
gctgcctacg ctattagcca gattctc                                         27

<210> SEQ ID NO 46
<211> LENGTH: 27
<212> TYPE: DNA
<213> ORGANISM: Artificial
<220> FEATURE:
<223> OTHER INFORMATION: Oligonucleotide primer

<400> SEQUENCE: 46
aatagcgtag gcagccgata ccgcgtg                                         27

<210> SEQ ID NO 47
<211> LENGTH: 27
<212> TYPE: DNA
<213> ORGANISM: Artificial
<220> FEATURE:
<223> OTHER INFORMATION: Oligonucleotide primer

<400> SEQUENCE: 47
gccgaagtca ttagccagat tctcgag                                         27

<210> SEQ ID NO 48
<211> LENGTH: 27
<212> TYPE: DNA
<213> ORGANISM: Artificial
<220> FEATURE:
<223> OTHER INFORMATION: Oligonucleotide primer

<400> SEQUENCE: 48
gctaatgact tcggcagccg ataccgc                                         27

<210> SEQ ID NO 49
<211> LENGTH: 27
<212> TYPE: DNA
<213> ORGANISM: Artificial
<220> FEATURE:
<223> OTHER INFORMATION: Oligonucleotide primer

<400> SEQUENCE: 49
gccgaatgga ttagccagat tctcgag                                         27

<210> SEQ ID NO 50
<211> LENGTH: 27
<212> TYPE: DNA
<213> ORGANISM: Artificial
<220> FEATURE:
<223> OTHER INFORMATION: Oligonucleotide primer

<400> SEQUENCE: 50
gctaatccat tcggcagccg ataccgc                                         27

<210> SEQ ID NO 51
<211> LENGTH: 920
<212> TYPE: PRT
<213> ORGANISM: Trichoderma reesei

<400> SEQUENCE: 51

Met Leu Ser Asn Pro Leu Arg Arg Tyr Ser Ala Tyr Pro Asp Ile Ser
1               5                   10                  15

Ser Ala Ser Phe Asp Pro Asn Tyr His Gly Ser Gln Ser His Leu His

-continued

```
                    20                  25                  30
Ser Ile Asn Val Asn Thr Phe Gly Asn Ser His Pro Tyr Pro Met Gln
                35                  40                  45

His Leu Ala Gln His Ala Glu Leu Ser Ser Ser Arg Met Ile Arg Ala
        50                  55                  60

Ser Pro Val Gln Pro Lys Gln Arg Gln Gly Ser Leu Ile Ala Ala Arg
65                  70                  75                  80

Lys Asn Ser Thr Gly Thr Ala Gly Pro Ile Arg Arg Arg Ile Ser Arg
                85                  90                  95

Ala Cys Asp Gln Cys Asn Gln Leu Arg Thr Lys Cys Asp Gly Leu His
            100                 105                 110

Pro Cys Ala His Cys Ile Glu Phe Gly Leu Gly Cys Glu Tyr Val Arg
            115                 120                 125

Glu Arg Lys Lys Arg Gly Lys Ala Ser Arg Lys Asp Ile Ala Ala Gln
        130                 135                 140

Gln Ala Ala Ala Ala Ala Gln His Ser Gly Gln Val Gln Asp Gly
145                 150                 155                 160

Pro Glu Asp Gln His Arg Lys Leu Ser Arg Gln Gln Ser Glu Ser Ser
            165                 170                 175

Arg Gly Ser Ala Glu Leu Ala Gln Pro Ala His Asp Pro Pro His Gly
            180                 185                 190

His Ile Glu Gly Ser Val Ser Ser Phe Ser Asp Asn Gly Leu Ser Gln
            195                 200                 205

His Ala Ala Met Gly Gly Met Asp Gly Leu Glu Asp His His Gly His
        210                 215                 220

Val Gly Val Asp Pro Ala Leu Gly Arg Thr Gln Leu Glu Ala Ser Ser
225                 230                 235                 240

Ala Met Gly Leu Gly Ala Tyr Gly Glu Val His Pro Gly Tyr Glu Ser
            245                 250                 255

Pro Gly Met Asn Gly His Val Met Val Pro Pro Ser Tyr Gly Ala Gln
            260                 265                 270

Thr Thr Met Ala Gly Tyr Ser Gly Ile Ser Tyr Ala Ala Gln Ala Pro
        275                 280                 285

Ser Pro Ala Thr Tyr Ser Ser Asp Gly Asn Phe Arg Leu Thr Gly His
    290                 295                 300

Ile His Asp Tyr Pro Leu Ala Asn Gly Ser Ser Pro Ser Trp Gly Gln
305                 310                 315                 320

Ser Asp Leu Arg Tyr Pro Val Leu Glu Pro Leu Leu Pro His Leu Gly
            325                 330                 335

Asn Ile Leu Pro Val Ser Leu Ala Cys Asp Leu Ile Asp Leu Tyr Phe
            340                 345                 350

Ser Ser Ser Ser Ser Ala Gln Met His Pro Met Ser Pro Tyr Val Leu
        355                 360                 365

Gly Phe Val Phe Arg Lys Arg Ser Phe Leu His Pro Thr Asn Pro Arg
    370                 375                 380

Arg Cys Gln Pro Ala Leu Leu Ala Ser Met Leu Trp Val Ala Ala Gln
385                 390                 395                 400

Thr Ser Glu Ala Ser Phe Leu Thr Ser Leu Pro Ser Ala Arg Ser Lys
            405                 410                 415

Val Cys Gln Lys Leu Leu Glu Leu Thr Val Gly Leu Leu Gln Pro Leu
            420                 425                 430

Ile His Thr Gly Thr Asn Ser Pro Ser Pro Lys Thr Ser Pro Val Val
            435                 440                 445
```

-continued

```
Gly Ala Ala Ala Leu Gly Val Leu Gly Val Ala Met Pro Gly Ser Leu
    450             455             460

Asn Met Asp Ser Leu Ala Gly Glu Thr Gly Ala Phe Gly Ala Ile Gly
465             470             475             480

Ser Leu Asp Asp Val Ile Thr Tyr Val His Leu Ala Thr Val Val Ser
            485             490             495

Ala Ser Glu Tyr Lys Gly Ala Ser Leu Arg Trp Trp Gly Ala Ala Trp
            500             505             510

Ser Leu Ala Arg Glu Leu Lys Leu Gly Arg Glu Leu Pro Pro Gly Asn
            515             520             525

Pro Pro Ala Asn Gln Glu Asp Gly Glu Gly Leu Ser Glu Asp Val Asp
    530             535             540

Glu His Asp Leu Asn Arg Asn Asn Thr Arg Phe Val Thr Glu Glu Glu
545             550             555             560

Arg Glu Glu Arg Arg Ala Trp Trp Leu Val Tyr Ile Val Asp Arg
            565             570             575

His Leu Ala Leu Cys Tyr Asn Arg Pro Leu Phe Leu Leu Asp Ser Glu
            580             585             590

Cys Ser Asp Leu Tyr His Pro Met Asp Asp Ile Lys Trp Gln Ala Gly
            595             600             605

Lys Phe Arg Ser His Asp Ala Gly Asn Ser Ser Ile Asn Ile Asp Ser
    610             615             620

Ser Met Thr Asp Glu Phe Gly Asp Ser Pro Arg Ala Ala Arg Gly Ala
625             630             635             640

His Tyr Glu Cys Arg Gly Arg Ser Ile Phe Gly Tyr Phe Leu Ser Leu
            645             650             655

Met Thr Ile Leu Gly Glu Ile Val Asp Val His His Ala Lys Ser His
            660             665             670

Pro Arg Phe Gly Val Gly Phe Arg Ser Ala Arg Asp Trp Asp Glu Gln
    675             680             685

Val Ala Glu Ile Thr Arg His Leu Asp Met Tyr Glu Glu Ser Leu Lys
    690             695             700

Arg Phe Val Ala Lys His Leu Pro Leu Ser Ser Lys Asp Lys Glu Gln
705             710             715             720

His Glu Met His Asp Ser Gly Ala Val Thr Asp Met Gln Ser Pro Leu
            725             730             735

Ser Val Arg Thr Asn Ala Ser Ser Arg Met Thr Glu Ser Glu Ile Gln
            740             745             750

Ala Ser Ile Val Val Ala Tyr Ser Thr His Val Met His Val Leu His
            755             760             765

Ile Leu Leu Ala Asp Lys Trp Asp Pro Ile Asn Leu Leu Asp Asp Asp
    770             775             780

Asp Leu Trp Ile Ser Ser Glu Gly Phe Val Thr Ala Thr Ser His Ala
785             790             795             800

Val Ser Ala Ala Glu Ala Ile Ser Gln Ile Leu Glu Phe Asp Pro Gly
            805             810             815

Leu Glu Phe Met Pro Phe Phe Tyr Gly Val Tyr Leu Leu Gln Gly Ser
            820             825             830

Phe Leu Leu Leu Leu Ile Ala Asp Lys Leu Gln Ala Glu Ala Ser Pro
    835             840             845

Ser Val Ile Lys Ala Cys Glu Thr Ile Val Arg Ala His Glu Ala Cys
    850             855             860
```

-continued

```
Val Val Thr Leu Ser Thr Glu Tyr Gln Arg Asn Phe Ser Lys Val Met
865             870             875                 880

Arg Ser Ala Leu Ala Leu Ile Arg Gly Arg Val Pro Glu Asp Leu Ala
            885             890                 895

Glu Gln Gln Gln Arg Arg Arg Glu Leu Leu Ala Leu Tyr Arg Trp Thr
            900             905             910

Gly Asn Gly Thr Gly Leu Ala Leu
            915             920
```